US010532069B2

(12) United States Patent
Story et al.

(10) Patent No.: US 10,532,069 B2
(45) Date of Patent: *Jan. 14, 2020

(54) COMPOSITIONS AND METHODS FOR TREATING JOINTS

(71) Applicant: DePuy Synthes Products, Inc., Raynham, MA (US)

(72) Inventors: Brooks J. Story, Franklin, MA (US); Scott A. Wadsworth, New Hope, PA (US); William R. Parrish, Hudson, MA (US); Uri Herzberg, Doylestown, PA (US); Donna Torres, Attleboro, MA (US); Benjamin A. Byers, North Easton, MA (US); Julia Hwang, Wayland, MA (US); Dongling Su, Franklin, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/612,267

(22) Filed: Jun. 2, 2017

(65) Prior Publication Data

US 2017/0266221 A1 Sep. 21, 2017

Related U.S. Application Data

(63) Continuation of application No. 14/600,770, filed on Jan. 20, 2015, now Pat. No. 9,682,099.

(51) Int. Cl.
| | | |
|---|---|---|
| *A61K 31/737* | (2006.01) | |
| *A61K 31/728* | (2006.01) | |
| *C08B 37/00* | (2006.01) | |
| *A61K 9/00* | (2006.01) | |
| *A61K 31/7016* | (2006.01) | |
| *A61K 31/726* | (2006.01) | |
| *A61K 47/36* | (2006.01) | |
| *A61L 27/50* | (2006.01) | |
| *A61M 5/315* | (2006.01) | |
| *C08B 37/08* | (2006.01) | |
| *A61L 27/20* | (2006.01) | |

(52) U.S. Cl.
CPC .......... *A61K 31/737* (2013.01); *A61K 9/0019* (2013.01); *A61K 31/7016* (2013.01); *A61K 31/726* (2013.01); *A61K 47/36* (2013.01); *A61L 27/20* (2013.01); *A61L 27/50* (2013.01); *A61M 5/31596* (2013.01); *C08B 37/0069* (2013.01); *C08B 37/0072* (2013.01); *A61L 2300/236* (2013.01); *A61L 2400/06* (2013.01); *A61L 2430/24* (2013.01)

(58) Field of Classification Search
None
See application file for complete search history.

(56) References Cited

U.S. PATENT DOCUMENTS

| | | | |
|---|---|---|---|
| 3,107,605 A | 10/1963 | Aldrich et al. |
| 3,454,560 A | 7/1969 | Nagasawa |
| 3,697,652 A | 10/1972 | Rovati et al. |
| 4,141,973 A | 2/1979 | Balazs |
| 4,666,897 A | 5/1987 | Golub et al. |
| 5,011,691 A | 4/1991 | Oppermann et al. |
| 5,143,724 A | 9/1992 | Leshchiner et al. |
| 5,171,579 A | 12/1992 | Ron et al. |
| 5,258,371 A | 11/1993 | Golub et al. |
| 5,266,683 A | 11/1993 | Oppermann et al. |
| 5,273,056 A | 12/1993 | McLaughlin et al. |
| 5,364,845 A | 11/1994 | Henderson |
| 5,366,964 A | 11/1994 | Lindstrom et al. |
| 5,380,716 A | 1/1995 | Conrad et al. |
| 5,399,351 A | 3/1995 | Leshchiner et al. |
| 5,409,904 A | 4/1995 | Hecht et al. |
| 5,498,606 A | 3/1996 | Soll et al. |
| 5,510,121 A | 4/1996 | Rhee et al. |
| 5,789,395 A | 8/1998 | Amin et al. |
| 5,792,103 A | 8/1998 | Schwartz et al. |
| 5,814,621 A | 9/1998 | Kanaya et al. |
| 6,030,635 A | 2/2000 | Gertzman et al. |
| 6,051,560 A | 4/2000 | Chang et al. |
| 6,069,135 A | 5/2000 | Falk et al. |
| 6,197,326 B1 | 3/2001 | Suzuki et al. |
| 6,238,372 B1 | 5/2001 | Zinger et al. |
| 6,281,195 B1 | 8/2001 | Rueger et al. |
| 6,288,043 B1 | 9/2001 | Spiro et al. |
| 6,346,519 B1 | 2/2002 | Petrus |

(Continued)

FOREIGN PATENT DOCUMENTS

| | | |
|---|---|---|
| CN | 101065106 A | 10/2007 |
| CN | 101112378 A | 1/2008 |

(Continued)

OTHER PUBLICATIONS

Pigman et al., Factors Affecting the Viscosity of Hyaluronic Acid and Synovial Fluid Archives of Biochemistry and Biophysics vol. 89 pp. 184-193 (Year: 1960).*
Gura et al., "Specific degradation of rheological hyaluronic acid and its properties" Polymer Degradation and Stability vol. 59 pp. 297-302 (Year: 1998).*
U.S. Appl. No. 12/979,972, filed Dec. 28, 2010, Compositions and methods for treating joints.
U.S. Appl. No. 12/979,981, filed Dec. 28, 2010, Compositions and methods for treating joints.
U.S. Appl. No. 12/979,990, filed Dec. 28, 2010, Compositions and methods for treating joints.
U.S. Appl. No. 13/173,658, filed Jun. 30, 2011, Compositions and methods for stabilized polysaccharide formulations.

(Continued)

*Primary Examiner* — Eric Olson

(57) ABSTRACT

Compositions and methods are disclosed for the treatment of osteoarthritis. The compositions comprising combinations of hyaluronic acid, glucosamine, and chondroitin sulfate, can be useful for any synovial joint, including the knee, shoulder, hip, ankle, hands, spinal facet, or temporomandibular joint, both for the relief of pain and for slowing disease progression.

20 Claims, 6 Drawing Sheets

(56) References Cited

U.S. PATENT DOCUMENTS

| | | |
|---|---|---|
| 6,410,044 B1 | 6/2002 | Chudzik et al. |
| 6,428,804 B1 | 8/2002 | Suzuki et al. |
| 6,437,018 B1 | 8/2002 | Gertzman et al. |
| 6,458,375 B1 | 10/2002 | Gertzman et al. |
| 6,551,801 B1 | 4/2003 | Andou et al. |
| 6,586,406 B2 | 7/2003 | Heidaran et al. |
| 6,608,043 B1 | 8/2003 | Serizawa et al. |
| 6,645,945 B1 * | 11/2003 | Radomsky ............ A61K 31/715 514/17.1 |
| 6,656,925 B2 | 12/2003 | Petrus |
| 6,677,321 B1 | 1/2004 | Levin |
| 6,699,471 B2 | 3/2004 | Radice et al. |
| RE38,522 E | 5/2004 | Gertzman et al. |
| 6,756,358 B2 | 6/2004 | Iwamoto et al. |
| 6,818,629 B2 | 11/2004 | Peterson et al. |
| 6,835,377 B2 | 12/2004 | Goldberg et al. |
| 6,906,044 B2 | 6/2005 | Hermida Ochoa |
| 6,911,212 B2 | 6/2005 | Gertzman et al. |
| 6,924,273 B2 | 8/2005 | Pierce |
| 6,924,370 B2 | 8/2005 | Chudzik et al. |
| 6,949,525 B2 | 9/2005 | Hermida |
| 6,972,321 B1 | 12/2005 | Hotten et al. |
| 6,979,679 B2 | 12/2005 | Marcum |
| 7,019,192 B2 | 3/2006 | Gertzman et al. |
| 7,025,959 B1 | 4/2006 | Hotten et al. |
| 7,026,292 B1 | 4/2006 | Lee et al. |
| 7,045,141 B2 | 5/2006 | Merboth et al. |
| 7,067,144 B2 | 6/2006 | Demopulos et al. |
| 7,070,942 B2 | 7/2006 | Heidaran et al. |
| 7,112,578 B2 | 9/2006 | Levin |
| 7,141,545 B2 | 11/2006 | Pike et al. |
| 7,189,392 B1 | 3/2007 | Kim et al. |
| RE39,587 E | 4/2007 | Gertzman et al. |
| 7,214,667 B2 | 5/2007 | Fukuda et al. |
| 7,223,744 B2 | 5/2007 | Yerxa et al. |
| 7,239,908 B1 | 7/2007 | Alexander et al. |
| 7,268,114 B2 | 9/2007 | Makishima et al. |
| 7,314,636 B2 | 1/2008 | Caseres et al. |
| 7,323,445 B2 | 1/2008 | Zhang et al. |
| 7,351,798 B2 | 4/2008 | Margolin et al. |
| 7,378,115 B2 | 5/2008 | Seipel |
| 7,425,573 B2 | 9/2008 | Pelletier et al. |
| 7,435,432 B2 | 10/2008 | Olson |
| 7,485,629 B2 | 2/2009 | Marcum |
| 7,582,311 B1 | 9/2009 | Cleland et al. |
| 7,592,009 B2 | 9/2009 | Hubbell et al. |
| 7,608,580 B2 | 10/2009 | Kim et al. |
| 7,651,682 B2 | 1/2010 | Devore et al. |
| 7,651,703 B2 | 1/2010 | Cleland et al. |
| 7,763,116 B2 | 7/2010 | Carter et al. |
| 7,931,030 B2 | 4/2011 | Bailleul |
| 8,398,611 B2 | 3/2013 | Hwang et al. |
| 8,623,839 B2 | 1/2014 | Su et al. |
| 9,682,099 B2 | 6/2017 | Story et al. |
| 2003/0031697 A1 | 2/2003 | Chudzik et al. |
| 2003/0086899 A1 | 5/2003 | Jafari |
| 2003/0181371 A1 | 9/2003 | Hunter et al. |
| 2003/0223983 A1 | 12/2003 | Sofia et al. |
| 2004/0038929 A1 | 2/2004 | Fukuda et al. |
| 2004/0082540 A1 | 4/2004 | Hermida Ochoa |
| 2004/0127402 A1 | 7/2004 | Vad |
| 2004/0147466 A1 | 7/2004 | Barman et al. |
| 2004/0214793 A1 | 10/2004 | Hermida Ochoa |
| 2004/0241248 A1 | 12/2004 | Margalit et al. |
| 2005/0025765 A1 | 2/2005 | DiMauro et al. |
| 2005/0079590 A1 | 4/2005 | Saha |
| 2005/0100538 A1 | 5/2005 | Mohamed et al. |
| 2005/0112186 A1 | 5/2005 | Devore et al. |
| 2005/0232981 A1 | 10/2005 | Ben-Sasson |
| 2005/0250737 A1 | 11/2005 | Hughes et al. |
| 2006/0040894 A1 | 2/2006 | Hunter et al. |
| 2006/0073207 A1 | 4/2006 | Masters et al. |
| 2006/0110459 A1 * | 5/2006 | Jafari ................ A61K 9/0019 424/488 |
| 2006/0122147 A1 | 6/2006 | Wohlrab |
| 2006/0122150 A1 | 6/2006 | Argentieri et al. |
| 2006/0210552 A1 | 9/2006 | Demopulos et al. |
| 2007/0053987 A1 | 3/2007 | Bayer et al. |
| 2007/0149441 A1 | 6/2007 | Aeschlimann et al. |
| 2007/0172517 A1 | 7/2007 | Ben-Sasson et al. |
| 2007/0190149 A1 | 8/2007 | Zahos |
| 2007/0203095 A1 | 8/2007 | Sadozai et al. |
| 2007/0275055 A1 | 11/2007 | Ben-Sasson et al. |
| 2007/0286881 A1 | 12/2007 | Burkinshsw |
| 2008/0003257 A1 | 1/2008 | Marcum et al. |
| 2008/0118523 A1 | 5/2008 | Hubbell et al. |
| 2008/0145404 A1 | 6/2008 | Hill et al. |
| 2008/0147065 A1 | 6/2008 | McKay et al. |
| 2008/0147077 A1 | 6/2008 | Garigapati et al. |
| 2008/0167235 A1 | 7/2008 | Zhang et al. |
| 2009/0017091 A1 | 1/2009 | Daniloff et al. |
| 2009/0017093 A1 | 1/2009 | Springer et al. |
| 2009/0035315 A1 | 2/2009 | Christgau et al. |
| 2009/0087503 A1 | 4/2009 | Henderson et al. |
| 2009/0099089 A1 | 4/2009 | Zhang et al. |
| 2009/0104148 A1 | 4/2009 | Jay et al. |
| 2009/0118348 A1 | 5/2009 | Miyamoto et al. |
| 2009/0123547 A1 | 5/2009 | Hill et al. |
| 2009/0124552 A1 | 5/2009 | Hill et al. |
| 2009/0136576 A1 | 5/2009 | Calvosa et al. |
| 2009/0162351 A1 | 6/2009 | Brown et al. |
| 2009/0162376 A1 | 6/2009 | Brown et al. |
| 2009/0181007 A1 | 7/2009 | Gennero et al. |
| 2009/0181058 A1 | 7/2009 | Li et al. |
| 2009/0202430 A1 | 8/2009 | Hoemann et al. |
| 2009/0202642 A1 | 8/2009 | Huang et al. |
| 2009/0291112 A1 | 11/2009 | Truncale et al. |
| 2010/0210584 A1 * | 8/2010 | Borge ................ A61K 31/7008 514/54 |
| 2010/0217231 A1 | 8/2010 | Ilan et al. |
| 2012/0165257 A1 | 6/2012 | Byers et al. |
| 2012/0165731 A1 | 6/2012 | Byers et al. |
| 2012/0165787 A1 | 6/2012 | Hwang et al. |
| 2013/0005681 A1 | 1/2013 | Su et al. |
| 2013/0172255 A1 | 7/2013 | Byers et al. |
| 2013/0178827 A1 | 7/2013 | Hwang et al. |
| 2014/0066389 A1 | 3/2014 | Eek |
| 2014/0088038 A1 | 3/2014 | Su et al. |
| 2014/0343012 A1 | 11/2014 | Hwang et al. |
| 2015/0190469 A1 | 7/2015 | Byers et al. |
| 2016/0206649 A1 | 7/2016 | Story et al. |
| 2018/0311272 A1 | 11/2018 | Hwang et al. |

FOREIGN PATENT DOCUMENTS

| | | |
|---|---|---|
| CN | 100594029 C | 3/2010 |
| DE | 202007011252 U1 | 12/2007 |
| EP | 0517970 A1 | 12/1992 |
| EP | 1005874 A1 | 6/2000 |
| EP | 2033689 A1 | 3/2009 |
| EP | 2251359 A1 | 11/2010 |
| FR | 2866571 A1 | 8/2005 |
| JP | 5452194 U | 4/1979 |
| JP | H09208476 A | 8/1997 |
| JP | 11302197 A | 11/1999 |
| JP | 2000212204 A | 8/2000 |
| JP | 2003501381 A | 1/2003 |
| JP | 2003160464 A | 6/2003 |
| JP | 2004359629 A | 12/2004 |
| JP | 2005-516027 A | 6/2005 |
| JP | 3748970 B2 | 2/2006 |
| JP | 2010530896 A | 9/2010 |
| JP | 2010540066 A | 12/2010 |
| KR | 20080024426 A | 3/2008 |
| WO | WO-9428889 A1 | 12/1994 |
| WO | WO-9621030 A1 | 7/1996 |
| WO | WO-9724374 A1 | 7/1997 |
| WO | WO-9728788 A1 | 8/1997 |
| WO | WO-98022114 A1 | 5/1998 |
| WO | WO-9940926 A1 | 8/1999 |
| WO | WO-03017826 A2 | 3/2003 |
| WO | WO-03034993 A2 | 5/2003 |
| WO | WO-03043660 A2 | 5/2003 |
| WO | WO-2004032943 A1 | 4/2004 |

(56) References Cited

FOREIGN PATENT DOCUMENTS

| WO | WO-2005110439 A2 | 11/2005 |
|---|---|---|
| WO | WO-2008098019 A2 | 8/2008 |
| WO | WO-2009005790 A2 | 1/2009 |
| WO | WO-2009024670 A2 | 2/2009 |
| WO | WO-2009132228 A1 | 10/2009 |
| WO | WO-2011086458 A1 | 7/2011 |

OTHER PUBLICATIONS

U.S. Appl. No. 13/750,148, filed Jan. 25, 2013, Compositions and methods for treating joints.
U.S. Appl. No. 13/788,838, filed Mar. 7, 2013, Methods for forming compositions for treating joints comprising bone morphogenetic protein and hyaluronic acid.
U.S. Appl. No. 14/090,599, filed Nov. 26, 2013, Compositions and methods for stabilized polysaccharide formulations.
U.S. Appl. No. 14/287,809, filed May 27, 2014, Compositions and methods for treating joints.
U.S. Appl. No. 14/559,319, filed Dec. 3, 2014, Compositions for Treating Joints Comprising Bone Morphogenetic Protein and Hyaluronic Acid.
U.S. Appl. No. 14/600,770, filed Jan. 20, 2015, Compositions and Methods for Treating Joints.
Japanese Office Action for Application No. 2016-175315, dated Jul. 18, 2017.
European Search Report for Application No. 17185327.8 dated Nov. 16, 2017.
Ko et al., Type II collagen-chondroitin sulfate-hyaluronan scaffold cross-linked by genipin for cartilage tissue engineering. J Biosci Bioeng. Feb. 2009;107(2):177-82.
Tokita et al., Degradation of hyaluronic acid during freeze drying. Polymer Degradation and Stability. 1997;55(2):159-64.
Michaels et al., "Dual Chamber Prefill Syringes" PDA Journal of Pharmaceutical Science and Technology, vol. 42, No. 6, pp. 199-202 (1988).
Yoshizane, Chiyo et al., "Trehalose suppresses osteoclast differentiation in ovariectomized mice: Correlation with decreased in vitro interleukin-6 production by bone marrow cells," Nutrition Research, vol. 20.10 (2000):1485-1491.
[No author listed] Greenfield Pharmacy, 1999, pp. 1-2.
[No Author Listed] Orthovisc® detailed product information. Jun. 2005, 2 pages. Retrieved Apr. 25, 2012 from <http://www.depuy.com/sites/default/files/products/files/OrthoviscNonAvianPIFinal2010.pdf>.
Wharton, K.A. et al., "*Drosophila* 60A gene, another transforming growth factor beta family member, is closely related to human bone morphogenetic proteins," Proc. Natl. Acad. Sci. USA, vol. 88.20 (1991):9214-9218.
[No Author Listed] Shiseido. Sodium Hyaluronate. Medical Grade. 1993, 4 pages.
[No Author Listed] The National Formulary XIV., 14th ed. Washington: American Pharmaceutical Association, 1975.
[No author listed] United Sugars Corporation, 2010, p. 1.
Barbucci et al., Hyaluronic acid hydrogel in the treatment of osteoarthritis. Biomaterials. Dec. 2002;23(23):4503-13.
Benaroudj, Nadia et al., "Trehalose Accumulation during Cellular Stress Protects Cells and Cellular Proteins from Damage by Oxygen Radicals," The Journal of Biological Chemistry, vol. 276 (2001):24261-24267.
Birch, G.G., "Trehaloses," Advances in Carbohydrate Chem., vol. 18 (1963):201-225.
Celeste, A.J. et al., "Identification of transforming growth factor beta family members present in bone-inductive protein purified from bovine bones," Proc. Natl. Acad. Sci. USA, vol. 87.24 (1990):9843-9847.
Chen, J.K. et al., "N-Acetylglucosamine: Production and Applications," Marine Drugs, vol. 8.9 (2010):2493-2516.
Chen, Q. et al., "Role of trehalose phosphate synthase and trehalose during hypoxia: from flies to mammals," J. Exp. Biol., vol. 207:Pt. 18 (2004):3125-3129.
Cheng, H. et al., "Osteogenic activity of the fourteen types of human bone morphogenetic proteins (BMPs)," The Journal of Bone and Joint Surgery Am., vol. 85-A.8 (2003):1544-1552.
Chinese Office Action dated Jul. 25, 2016 for Application No. 201210223133.6.
Chinese Office Action dated Sep. 26, 2016 for Application No. 201410211992.2.
Communication of a notice of opposition issued in European Application No. 11195499.6 dated Aug. 7, 2014.
European Partial Search Report for Application No. 12174614.3, dated Aug. 14, 2012. (9 pages).
European Search Report dated Jul. 7, 2016 for Application No. 16151940.0 (7 pages).
Extended European Search Report dated Mar. 20, 2012 for Application No. 11195499.6 (5 pages).
Gilman et al., eds., Goodman and Gilman's: The Pharmacological Basis for Therapeutics. Table of contents. 4 pages. Seventh Edition, 1985, Macmillan Publishers, London.
Hoelzle, I. et al., "Increased Accumulation of Trehalose in Rhizobia Cultured under 1% Oxygen," Applied and Environmental Microbiology, vol. 56.10 (1990)3213-3215.
Honda, J. et al., "Direct refolding of recombinant human growth differentiation factor 5 for large-scale production process," Journal of Bioscience and Bioengineering, vol. 89.6 (2000):582-589.
Indian Examination Report dated Aug. 13, 2015 for Application No. 3778/DEL/2011 (3 pages).
Japanese Office Action dated Dec. 8, 2015 for Application No. 2011-285276.
Liang et al. The relationship; between low pH in intervertebral discs and low back pain: a systematic review.; Arch Med Sci. Dec. 20, 2012;8(6):952-6.
Lyons, K. et al., "Vgr-1, a mammalian gene related to Xenopus Vg-1, is a member of the transforming growth factor beta gene superfamily," Proc. Natl. Acad. Sci. USA, vol. 86.12 (1989):4554-4558.
Maleki et al., Effect of pH on the Behavior of Hyaluronic Acid in Dilute and Semidilute Aqueous Solutions. Macromolecular Symposia. Dec. 1, 2008;274(1):131-140.
Mankin, H.J. et al., "The glycosaminoglycans of normal and arthritic cartilage," The Journal of Clinical Investigation, vol. 50.8 (1971):1712-1719.
Massague, Joan, "The Transforming Growth Factor-beta Family," Annu. Rev. Cell Biol., vol. 6 (1990):597-641.
Minutoli, L. et al., "The disaccharide trehalose inhibits proinflammatory phenotype activation in macrophages and prevents mortality in experimental septic shock," SHOCK, vol. 27.1 (2007):91-96.
Ozkaynak, E. et al., "OP-1 cDNA encodes an osteogenic protein in the TGF-beta family," The EMBO Journal, vol. 9.7 (1990):2085-2093.
*Pharmaceutics: The Science of Dosage Form Design*. Aulton, ed. London: Churchill Livingston. 2nd ed. (2002):390-393.
Rabago et al., Hypertonic dextrose injections (prolotherapy) for knee; osteoarthritis: results of a single-arm uncontrolled study with 1-year follow-up.; J Altern Complement Med. Apr. 2012;18(4):408-14.
Remington's Pharmaceutical Sciences, 15th ed. Easton: Mack Publishing Co., pp. 1405-1412, 1461-1487 (1975).
Rohanizadeh, R. et al., "Hydroxyapatite as a carrier for bone morphogenetic protein," The Journal of Oral Implantology, vol. 37.6 (2011):659-672.
Ruppert, R. et al., "Human bone morphogenetic protein 2 contains a heparin-binding site which modifies its biological activity," European Journal of Biochemistry, vol. 237.1 (1996):295-302.
Sampath, T.K. et al., "Bovine osteogenic protein is composed of dimers of OP-1 and BMP-2A, two members of the transforming growth factor-beta superfamily," The Journal of Biological Chemistry, vol. 265.22 (1990):13198-13205.
Vejlens, Lars, "Glycosaminoglycans of human bone tissue," Calcified Tissue Research 1971, vol. 7, Issue 1, pp. 175-190.

(56) References Cited

OTHER PUBLICATIONS

Frisbie et al., "Evaluation of intra-articular hyaluronan, sodium chondroitin sulfate and N-acetyl-o-glucosamine combination versus saline (0.9% NaCI) for osteoarthritis using an equine model." The Veterinary Journal, vol. 197 (2013): 324-829.

Polyglycan® Product Information. IC Bimeda, www.BimedaUS.com, Sep. 2017 (3 pages).

Polyglycan®-HV Product Information. IC Bimeda, www.BimedaUS.com, Sep. 2017 (3 pages).

Polyglycan®-SA Product Information. IC Bimeda, www.BimedaUS.com, Sep. 2017 (3 pages).

Orthovisc Product Information. DePuy Synthes, Mitek Sports Medicine, DePuy Mitek, Inc., www.depuysynthes.com, Sep. 2014 (9 pages).

Hu, R. (Ed.) "Industrial Pharmaceutics,"China Herbal Medicine Press, Aug. 31, 2010, pp. 426-434.

Chen, J. (Ed.),"365 questions in prevention and treatment of common rheumatism,"May 31, 2013, pp. 235-255.

Wang, R. (Ed.),"Pharmaceutics,"Peoples's Hygiene Press, Oct. 31, 2000, pp. 255-260.

Translation of Chinese Search Report for CN Application 201610037012 dated Sep. 26, 2019 (2 pages).

\* cited by examiner

Gait Analysis Score (2nd reactivation)

COMPOSITIONS AND METHODS FOR TREATING JOINTS

CROSS-REFERENCE TO RELATED APPLICATIONS

This application is a continuation of U.S. patent application Ser. No. 14/600,770 filed on Jan. 20, 2015, entitled "Compositions and Methods for Treating Joints, which is hereby incorporated by reference in its entirety.

FIELD

The present disclosure relates generally to compositions and methods for treating joints.

BACKGROUND

Osteoarthritis ("OA"), the most common form of arthritis, is a type of arthritis that is characterized by degenerative (gradual deterioration of joint) or abnormal changes in bone, cartilage, and synovium of the joints. OA is often characterized by a progressive wearing down of opposing joint surfaces accompanied at times by inflammation resulting in pain, swelling, and stiffness for the patient. OA can occur in one or more joints following trauma to the joint, following an infection of the joint, or simply as a result of aging. Furthermore, there is emerging evidence that abnormal anatomy may contribute to early development of OA. In the US alone, over 25 million people are estimated to have radiographic OA of the knee, with 16 million of those suffering from symptomatic OA. The prevalence of OA is increasing rapidly, in part due to an aging population that is more active, as well as an increasingly obese general population.

Treatment of OA generally involves a combination of exercise or physical therapy, lifestyle modification, and analgesics. Acetaminophen is typically the first line of treatment for OA. For mild to moderate symptoms, effectiveness is similar to non-steroidal anti-inflammatory drugs ("NSAIDs"), such as ibuprofen. For more severe symptoms, NSAIDs may be more effective. However, while more effective, NSAIDs in severe cases are associated with greater side effects such as gastrointestinal bleeding and renal complications. Another class of NSAIDs, COX-2 selective inhibitors (such as Celecoxib), is equally effective as NSAIDs but no safer in terms of side effects. There are several NSAIDs available for topical use, including diclofenac. Typically, they have less systemic side-effects than oral administration and at least some therapeutic effects. While opioid analgesics, such as morphine and fentanyl, improve pain, this benefit is outweighed by frequent adverse events and thus they are not routinely used.

Intra-articular steroid injections are also used in the treatment of OA, and they are very effective at providing pain relief. However, the durability of the pain relief is limited to 4-6 weeks and there are adverse effects that may include collateral cartilage damage. If pain becomes debilitating, joint replacement surgery may be used to improve mobility and quality of life. There is no proven treatment to slow or reverse the disease.

For patients who do not get adequate pain relief from simple pain relievers, like acetaminophen or from exercise and physical therapy, intra-articular injections of hyaluronic acid (HA) provide another treatment option to address symptomatic pain and delay the need for a total joint replacement surgery. It is known that the concentration of native HA is deficient in individuals suffering from OA and therefore joint injections of exogenous HA is believed to replenish these molecules and restore the viscoelastic properties of synovial fluid. It is this property that is responsible for lubricating and cushioning the joints. There is also evidence that HA has biological activity through binding to cell surface receptors and may have a role in mitigating inflammation. Independent of the mechanism of action, pain relief is observed for about six months following a treatment course. A treatment course for HA products on the US market can range from single injection product to others that require 3 to 5 weekly injections to attain this durability of pain relief. In using intra-articular injections, it is well-known that a neutral pH and an isotonic solution are preferred to avoid pain with injection and joint or tissue damage. The desire for a neutral and isotonic solution can limit the type and concentration of drugs that can be injected.

While the above therapies can provide at least a partial relief of OA pain, there are no approved therapies that can slow or halt the progression of the disease in humans. Accordingly, there remains a need for improved methods and compositions for treating OA in joints, and to address the pain and structural degeneration associated with OA.

SUMMARY

Provided herein are compositions and methods for treating joint conditions, such as osteoarthritis and/or the pain associated therewith. In one embodiment, a composition for treating joints is provided and includes a first component hyaluronic acid (HA), a second component, glucosamine, and a third component, chondroitin sulfate. The composition can have a pH in the range of about 3-5 and an osmolality in the range of about 330-750 mOSM. The composition can be injectable. It is surprising that the most effective injectable solution for treating joints is both acidic and hypertonic, both of which would be expected to cause pain, irritation, and inflammation. As demonstrated herein, hyaluronic acid combined with glucosamine and chondroitin sulfate overcomes the pain, irritation and inflammation typically associated with an injection of low pH and high osmolality used herein.

The concentration of the components can vary. In one embodiment, glucosamine is present in a concentration of about 0.005-54 mg/mL. In one embodiment, chondroitin sulfate is present in a concentration of about 0.005-54 mg/mL. In one embodiment, hyaluronic acid is present in a concentration of about 3.6-36 mg/mL. In one embodiment, when the components are combined to form a composition, the glucosamine and chondroitin sulfate are present within the composition at a ratio of about 1:1 by weight.

In one exemplary embodiment, the composition includes about 18-20 mg/mL of glucosamine, about 18-20 mg/mL of chondroitin sulfate, about 12-17.5 mg/mL of hyaluronic acid; and the composition has a pH value of 3.5-4 and an osmolality of about 600-650 mOSM.

The composition can also include an additional component, such as a stabilizer. In another embodiment, the additional component can be trehalose.

In other aspects, a method for treating joints is provided and includes injecting a therapeutically effective amount of a formulation into a joint of a subject, where the formulation comprises hyaluronic acid (HA), glucosamine, and chondroitin sulfate. The formulation can have a pH of about 3-5 and an osmolality of about 330-750 mOSM. In an exemplary embodiment, the HA is combined with a mixture of glucosamine and chondroitin sulfate no more than about 60 minutes prior to injection, and more typically, no more than about 30 minutes prior to injection.

The concentration of the components in the formulation used in the method can vary. In one embodiment, glucosamine is present in a concentration of about 0.005-54 mg/mL. In one embodiment, chondroitin sulfate is present in a concentration of about 0.005-54 mg/mL. In one embodiment, hyaluronic acid is present in a concentration of about 3.6-36 mg/mL. In one embodiment, when the components are combined to form a formulation, the glucosamine and chondroitin sulfate are present within the formulation at a ratio of about 1:1 by weight.

In one exemplary embodiment, the formulation includes about 18-20 mg/mL of glucosamine, about 18-20 mg/mL of chondroitin sulfate, about 12-17.5 mg/mL of hyaluronic acid; and the composition has a pH value of 3.5-4 and an osmolality of about 600-650 mOSM.

The formulation can also include an additional component, such as a stabilizer. In another embodiment, the additional component can be trehalose.

In one embodiment, a kit for treating joints is provided and includes a first component comprising hyaluronic acid and a second component comprising a mixture of glucosamine and chondroitin sulfate, and a syringe for injecting a mixture of the first and second components. The mixture of the first and second components can have a pH of about 3-5 and an osmolality of about 330-750 mOSM. The syringe can have various configurations, and in one embodiment the syringe has a first chamber containing the first component, a second container containing the second component, and a plunger configured to displace the second component from the second container into the first container, combine them, and form the formulation.

The kit can also include an additional component, such as a stabilizer. In some embodiments, one or more components can be lyophilized.

BRIEF DESCRIPTION OF THE DRAWINGS

The compositions, methods, and kits will be more fully understood from the following detailed description taken in conjunction with the accompanying drawings, in which.

Figure 1:
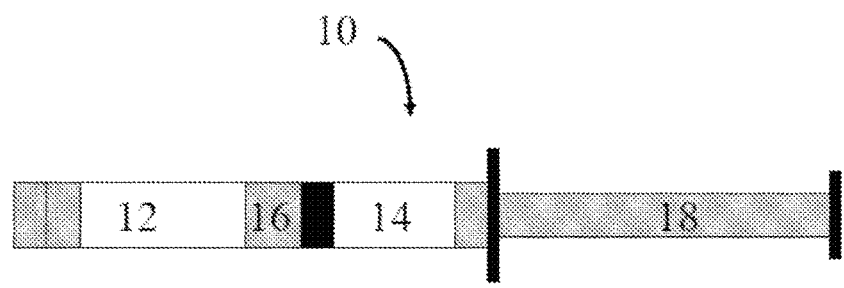
FIG. 1 is a schematic view of one embodiment of a mixing and delivery system for use with the present compositions and methods.

The appended drawings have been included herein so that the above-recited features, advantages and objects will become clear and can be understood in detail. These drawings form a part of the specification. It is to be noted, however, that the appended drawings illustrate exemplary embodiments and should not be considered to limit the scope.

DETAILED DESCRIPTION

Certain exemplary embodiments will now be described to provide an overall understanding of the principles of the compositions, formulations and methods disclosed herein. One or more examples of these embodiments are illustrated in the accompanying drawings. Those skilled in the art will understand that the compositions and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present disclosure.

A therapeutically effective amount or effective amount of the composition can be administered to achieve a pharmacological effect. The term "therapeutically effective amount" includes, for example, a prophylactically effective amount. An "effective amount" is an amount effective to achieve a desired pharmacologic effect or therapeutic improvement without undue adverse side effects. For example, an effective amount refers to an amount that increases operability, or increases weight bearing load, or decreases pain, or increases growth in the bone and cartilage of one or more joints, or reduces joint distortion, pain, swelling, or stiffness. The effective amount of an agent will be selected by those skilled in the art depending on the particular patient and the disease level. It is understood that "an effective amount" or "a therapeutically effective amount" can vary from subject to subject, due to variation in metabolism of therapeutic agents and/or prokinetic agents, age, weight, general condition of the subject, the condition being treated, the severity of the condition being treated, and the judgment of the prescribing physician.

"Treat" or "treatment" refers to any treatment of a disorder or disease associated with bone or cartilage disorder, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder. Thus, as used herein, the term "treat" is used synonymously with the term "prevent."

"Co-administered" means simultaneous administration in the same formulation or in two different formulations that are combined into one formulation for administration.

The term "subject" as used herein refers to an animal, such as a mammal and particularly a human who can benefit from the present compositions and methods. There is no limitation on the type of animal that could benefit from the present methods. A subject regardless of whether a human or non-human animal may be referred to as an individual, subject, animal, host or recipient. The methods disclosed herein have applications in human medicine, veterinary medicine as well as in general, domestic or wild animal husbandry. In some embodiments, the candidate subject is a mammal such as a human or laboratory test animal such as a mouse, rat, rabbit, guinea pig, hamster or avian species such as a poultry bird.

One skilled in the art will appreciate that the term "precipitation," as used herein, refers to the formation of an insoluble protein in the solution. In contrast to known examples of drugs that are delivered as a suspension (due to the fact that the carrier, e.g., a mineral, ceramic, metal, or polymeric, is insoluble rather than the active protein), an aspect disclosed herein is the active precipitation of the protein immediately prior to delivery of the composition to a patient.

In general, provided herein are compositions and methods for treating joint conditions, such as pain and degeneration associated with osteoarthritis. The compositions and methods utilize hyaluronic acid ("HA"), in combination with glucosamine and chondroitin sulfate in an injectable formulation with a low pH value and a high osmolality. In an exemplary embodiment, the glucosamine is in the form of glucosamine hydrochloride salt, glucosamine sulfate or N-acetyl-glucosamine. The composition can optionally include additional components including a stabilizer, such as trehalose, sucrose, raffinose, glucose, mannitol, sorbitol, erythritol or any combination thereof.

Surprisingly, the combination of HA with glucosamine and chondroitin sulfate overcomes the potential side effects associated with the low pH and high osmolality of the formulation. It is well-known in the art that neutral pH and isotonic solutions are preferred for injections to avoid pain and tissue degeneration. As a result, glucosamine is typically used in injections at a low concentration to allow for a neutral pH. Similarly, chondroitin sulfate is typically also used in injections at a low concentration to allow for an isotonic solution. Unexpectedly, the combination of hyaluronic acid, with glucosamine and chondroitin sulfate, enables the use of an injectable formulation with a low pH and high osmolality without causing any pain or tissue damage.

The composition can be administered to any synovial joint, including the knee, shoulder, hip, ankle, hands, spinal facet, or temporomandibular joint, both for the relief of pain and slowing of disease progression. The composition may include any of several combinations of hyaluronic acid, glucosamine, and chondroitin sulfate that can be delivered into the joint via an injection. Also provided herein are a kit for administration of an injection, and a method of administering the composition with or without the use of a kit.

Hyaluronic Acid

Hyaluronic acid (HA) can have various formulations and can be provided at various concentrations and molecular weights. The terms "hyaluronic acid," "hyaluronan," "hyaluronate," and "HA" are used interchangeably herein to refer to hyaluronic acid or salts of hyaluronic acid, such as the sodium, potassium, magnesium, and calcium salts, among others. These terms are also intended to include not only pure hyaluronic acid solutions, but hyaluronic acid with other trace elements or in various compositions with other elements. The terms "hyaluronic acid," "hyaluronan," and "HA" encompass chemical or polymeric or cross-linked derivatives of HA. Examples of chemical modifications which may be made to HA include any reaction of an agent with the four reactive groups of HA, namely the acetamido, carboxyl, hydroxyl, and the reducing end. The HA disclosed herein is intended to include natural formulations (isolated from animal tissue) or synthetic formulations (derived from bacterial fermentation) or combinations thereof. The HA can be provided in liquid form or in a solid formulation that is reconstituted with a diluent to achieve an appropriate concentration.

HA is a glycosaminoglycan (GAG), and in particular HA is an unbranched polysaccharide made up of alternating glucuronic acid and N-acetyl glucosamine units. In liquid form, the HA has viscoelastic properties. HA is also found in the extracellular matrix of cartilage as an important structural component of aggrecan, which makes up the proteoglycan complex. The major function of the proteoglycan complex is to retain water in the cartilage matrix, imparting its characteristic turgidity and mechanical resiliency.

HA not only helps to maintain healthy mechanical properties of cartilage that cushions joints, but it is also a major component of synovial fluid.

HA can be used in the compositions and methods described herein at various molecular weights. Since HA is a polymeric molecule, the HA component can exhibit a range of molecular weights, and almost any average of modal molecular weight formulation of HA can be used in the compositions and methods described herein, including Low Molecular Weight ("LWM") Hyaluronan (about 500 to 700 kilodaltons (kDa), Medium Molecular Weight ("MMW") Hyaluronan (700-1000 kDa), and High Molecular Weight ("HMW") Hyaluronan (1.0-6.0 million daltons (MDa)). In certain exemplary embodiments, the HA has a molecular weight of at least about 700 kDa, and in certain embodiments, the HA is a High Molecular Weight ("HWM") HA having a molecular weight of at least about 1 MDa. The molecular weight can be, for example, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000 kDa or more, or any range derivable therein. It is expected that chemically modified HA could have very different molecular weights than described above. A cross-linked HA can likewise have much higher molecular weight than noted above. Regardless, these materials are also applicable to the compositions and methods disclosed herein.

HA can be present in solid, lyophilized or liquid form. When in liquid form, solvents can be used to solubilize HA. Solvents can include, but are not limited to, water, saline or other salt solutions, buffer solutions such as phosphate buffered saline, histidine, lactate, succinate, glycine, and glutamate, dextrose, glycerol, as well as combinations thereof.

The concentration of HA present in the formulation can also vary, but in an exemplary embodiment HA is provided at a pharmaceutically effective amount. In one embodiment, the HA has a concentration of at least about 1 mg/mL. In an exemplary embodiment, the HA has a concentration of at least about 5 mg/mL, and more particularly at least about 7 mg/mL, and more particularly at least about 10 mg/mL, and more particularly at least about 12 mg/mL, and in some embodiments the concentration can be at least about 25 mg/mL. In some embodiments, the HA can have a concentration in the range of about 3.6 mg/mL to about 36 mg/mL. In another embodiment, the HA can have a concentration in the range of about 12 mg/mL to about 25 mg/mL. Suitable concentrations of HA include about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mg, 12 mg/mL, 12.5 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/1, 60 mg/mL or more or any range derivable therein.

In one embodiment, the first component comprises an HA having a high molecular weight (1 to 6 MDa) having a concentration in the range of about 5-40 mg/mL. One such product is Orthovisc® manufactured by Anika Therapeutics, Inc. of Bedford, Mass. Orthovisc® is a sterile, non-pyrogenic, clear, viscoelastic solution of hyaluronan. Orthovisc® consists of high molecular weight (1.0-2.9 MDa), ultra-pure natural hyaluronan dissolved in physiological saline and having a nominal concentrations between 12.5-17.5 mg/mL. Orthovisc® is isolated through bacterial fermentation. One skilled in the art will recognize that there are companies such as Shiseido and Lifecore who can produce high molecular weight HA through a bacterial fermentation process. Another example of an HA product available in the United States with these characteristics is Euflexxa®.

Glucosamine

Glucosamine ($C_6H_{13}NO_5$) ("GlcN") or its derivatives can also be included in the formulation to enhance synthesis of key components of cartilage and synovial fluid by feeding both reactions necessary for the production of hyaluronan as well as for proteoglycans. GlcN is an amino sugar carrying four hydroxyl groups and an amine group, and it is a prominent precursor in the biochemical synthesis of glycosylated proteins and lipids. GlcN is a naturally occurring molecule that has nutritive and effector functions. As used herein, "glucosamine" includes glucosamine salts, such as glucosamine hydrochloride and glucosamine sulfate, as well as non-salt forms such as N-acetylglucosamine. In one embodiment, glucosamine hydrochloride is included in the formulation.

GlcN is compatible with and promotes stem cell growth and differentiation of mesenchymal stem cells to form chondrocytes. GlcN can have a role in tissue development and repair, such as cartilage growth and development, in general. It is used as a nutritional supplement to combat the symptoms of OA, and has been shown slow cartilage destruction in clinical studies.

GlcN can be used in the compositions and methods disclosed herein as various different salts, or in non-salt forms such as N-acetyl-glucosamine. Exemplary GlcN used herein can be glucosamine hydrochloride, glucosamine sulfate or N-acetyl-glucosamine. The concentration range is discussed below.

Glucosamine can be present in solid, liquid, or lyophilized form. A person skilled in the art will appreciate that, while lyophilized glucosamine is particularly useful in exemplary embodiments, liquid glucosamine can also be used in the composition. For example, glucosamine can be obtained in powder form and mixed with a solvent, such as water, to form a solution. The solution can be combined with additional components to form a mixture. In an exemplary embodiment the glucosamine is lyophilized to allow for increased stability of the injectable composition.

The concentration of the GlcN used in the compositions, formulations and methods described herein can vary. A suitable local concentration can be at least about 180 mg/mL, about 170 mg/mL, about 160 mg/mL, about 150 mg/mL, about 140 mg/mL, about 130 mg/mL, about 120 mg/mL, about 110 mg/mL, about 100 mg/mL, about 90 mg/mL, about 80 mg/mL, about 70 mg/mL, about 60 mg/mL, about 50 mg/mL, about 40 mg/mL, about 38 mg/mL, about 36 mg/mL, about 34 mg/mL, about 32 mg/mL, 30 mg/mL, 28 mg/mL, 25 mg/mL, 22 mg/mL, 20 mg/mL, about 19 mg/mL, about 18.5 mg/mL, about 18 mg/mL, about 17.5 mg/mL, about 17 mg/mL, about 16 mg/mL, about 15 mg/mL, about 12 mg/mL, about 10 mg/mL, about 5.0 mg/mL, about 2.5 mg/mL, about 2.0 mg/mL, about 1.8 mg/mL, about 1.5 mg/mL, about 1.0 mg/mL, about 0.5 mg/mL, about 0.018 mg/mL, about 0.0018 mg/mL, about 0.00018 mg/mL, or so on. In some embodiments, a high dose of GlcN (e.g., about 180 mg/mL, about 170 mg/mL, about 160 mg/mL, about 150 mg/mL, about 140 mg/mL, about 130 mg/mL, about 120 mg/mL, about 110 mg/mL, about 100 mg/mL, about 90 mg/mL, about 80 mg/mL, about 70 mg/mL, about 60 mg/mL, about 50 mg/mL, about 40 mg/mL, about 38 mg/mL, about 36 mg/mL, about 34 mg/mL, about 32 mg/mL, 30 mg/mL, 28 mg/mL, 25 mg/mL, 22 mg/mL, 20 mg/mL, about 19 mg/mL, about 18.5 mg/mL, about 18 mg/mL) is used. In some embodiments, a low dose of GlcN (e.g., about 5.0 mg/mL, about 2.5 mg/mL, about 2.0 mg/mL, about 1.8 mg/mL, about 1.5 mg/mL, about 1.0 mg/mL, about 0.5 mg/mL, about 0.018 mg/mL, about 0.0018 mg/mL, about 0.00018 mg/mL or lower) is used. A person skilled in the art can determine a suitable local concentration of GlcN practicing methods known in the pharmaceutics art, and that determination will govern the nature and composition of the GlcN composition of interest to obtain the desired concentration of GlcN.

Chondroitin Sulfate

Chondroitin sulfate (CS), which is an essential component of cartilage, is composed of an alternating sequence of sulfated and/or unsulfated D-glucuronic acid (GlcA) and N-acetyl-D-galactosamine (GalNAc) residues linked through alternating β(1,3) and β(1,4) bonds. These compounds each have a polymeric structure consisting mainly of about 40 to 100 times repetition of the disaccharide units. CS can be used in the inventive formulation at various molecular weights and concentrations. CS can be isolated from bovine or marine sources. A chondroitin chain can have over 100 individual sugars, each of which can be sulfated in variable positions and quantities. Chondroitin-4 sulfate, also carbon 4 of the N-acetylgalactosamine (GalNAc) sugar, is found in nasal and tracheal cartilages of bovines and porcines. It is also found in the bones, flesh, blood, skin, umbilical cord, and urine of these animals. Chondroitin-6 sulfate, also carbon 6 of the GalNAc sugar, has been isolated from the skin, umbilical cord, and cardiac valves of these animals. Chondroitin-6 sulfate has the same composition, but slightly different physical properties from chondroitin-4 sulfate. Chondroitin sulfate is involved in the binding of collagen and is also directly involved in the retention of moisture. These are both properties that aid the healing process. A person skilled in the art will appreciate that the terms "chondroitin sulfate," "CS," "chondroitin," "chondroitin sulfuric acid," and "chonsurid" are used interchangeably herein and also encompass chemical or isomeric or cross-linked derivatives throughout this application.

CS can be present in the compositions and methods disclosed herein at various molecular weights. In certain exemplary embodiments the molecular weight is in the range about 5 to 1,000 kDa, in the range of about 6 to 500 kDa, in the range of about 7 to 300 kDa, in the range of about 8 to 200 kDa, in the range of about 9 to 100 kDa, or typically in the range of about 10 to 80 kDa.

CS can be present in solid, liquid, or lyophilized form. A person skilled in the art will appreciate that, while lyophilized CS is particularly useful in exemplary embodiments, liquid CS can also be used in the composition. For example, CS can be obtained in powder form and mixed with a solvent, such as water, to form a solution. The solution can be combined with additional components to form a mixture. Thus, while liquid, non-lyophilized CS compositions can be used with the present invention, in an exemplary embodiment, the CS is lyophilized to allow for increased stability of the injectable composition.

CS can be used in the compositions and methods described herein at various concentrations. The concentration of CS in the composition can also vary, but in an exemplary embodiment CS is provided at a pharmaceutically effective amount. A suitable local concentration can be at least about 80 mg/mL, about 75 mg/mL, about 70 mg/mL, about 65 mg/mL, about 60 mg/mL, about 55 mg/mL, about 50 mg/mL, about 45 mg/mL, about 40 mg/mL, about 38 mg/mL, about 36 mg/mL, about 34 mg/mL, about 32 mg/mL, 30 mg/mL, 28 mg/mL, 25 mg/mL, 22 mg/mL, 20 mg/mL, about 19 mg/mL, about 18.5 mg/mL, about 18 mg/mL, about 17.5 mg/mL, about 17 mg/mL, about 16 mg/mL, about 15 mg/mL, about 12 mg/mL, about 10 mg/mL, about 5.0 mg/mL, about 2.5 mg/mL, about 2.0 mg/mL, about 1.8 mg/mL, about 1.5 mg/mL, about 1.0 mg/mL, about 0.5 mg/mL, about 0.018 mg/mL, about 0.1 mg/mL, about 0.05 mg/mL, about 0.005 mg/mL, or so on. In some embodiments, a high dose of CS (e.g., about 80 mg/mL, about 75 mg/mL, about 70 mg/mL, about 65 mg/mL, about 60 mg/mL, about 55 mg/mL, about 50 mg/mL, about 45 mg/mL, about 40 mg/mL, about 38 mg/mL, about 36 mg/mL, about 34 mg/mL, about 32 mg/mL, 30 mg/mL, 28 mg/mL, 25 mg/mL, 22 mg/mL, 20 mg/mL, about 19 mg/mL, about 18.5 mg/mL, about 18 mg/mL) is used. In some embodiments, a low dose of CS (e.g., about 5.0 mg/mL, about 2.5 mg/mL, about 2.0 mg/mL, about 1.8 mg/mL, about 1.5 mg/mL, about 1.0 mg/mL, about 0.5 mg/mL, about 0.018 mg/mL, about 0.1 mg/mL, about 0.05 mg/mL, about 0.005 mg/mL or lower) is used. A person skilled in the art can determine a suitable local concentration of CS practicing methods known in the pharmaceutics art, and that determination will govern the nature and composition of the CS composition of interest to obtain the desired concentration of CS.

Additional Components

In an exemplary embodiment, at least one additional component can be added to the compositions and methods disclosed herein. A person skilled in the art will appreciate that the present compositions and methods can include various other joint treatment components, including, for example, amino acids, proteins, saccharides, disaccharides, polysaccharides, lipids, nucleic acids, buffers, surfactants, and mixtures thereof. Other useful components can include steroids, anti-inflammatory agents, non-steroidal anti-inflammatory agents, analgesics, cells, antibiotics, antimicrobial agents, anti-inflammatory agents, growth factors, growth factor fragments, small-molecule wound healing stimulants, hormones, cytokines, peptides, antibodies, enzymes, isolated cells, platelets, immunosuppressants, nucleic acids, cell types, viruses, virus particles, essential nutrients or vitamins, and combinations thereof.

Stabilizers can be used in the present methods and compositions. Stabilizers can be sugars or derivatives, such as saccharides, disaccharides, modified saccharides, sugar alcohols, or polysaccharides. In an exemplary embodiment, the stabilizer can be tocopherol, tocopherol derivatives, glucose, mannitol, sucrose and/or trehalose.

Buffering agents can also be added to the formulation to control pH. Examples of buffering agents can be any one or more of the following agents, and is not limited to, acetic acid, ammonium carbonate, ammonium phosphate, boric acid, citric acid, glycine, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, TRIS and sodium carbonate.

Additionally, isotonic agents can be added to control ionic concentration and/or osmotic pressure of the formulation. Examples of isotonic agents can be any one or more of the following agents, and is not limited to, dextrose, sucrose, trehalose, glycerin, mannitol, potassium chloride, sodium chloride.

Common stabilizers or stabilizing excipients used in the pharmaceutical industry are saccharides, disaccharides, modified saccharides, sugar alcohols and polysaccharides. In one embodiment, the formulation or composition includes at least one stabilizer or stabilizing excipient, such as tocopherol, tocopherol derivatives, mannitol, glucose, sucrose and trehalose. The stabilizers can be present in a range of about 0.1-70% by weight; about 0.1-50% by weight, about 0.1-20% by weight; or about 0.5-20% by weight. Alternatively, the excipient can be present at a concentration in a range of about 1 mg/mL to about 700 mg/mL, in a range of about 1 mg/mL to about 500 mg/mL, in a range of about 1 mg/mL to about 200 mg/mL, and more particularly in a range of about 5 mg/mL to about 200 mg/mL.

Tocopherol belongs to a class of chemical compounds that encompass mono, di and trimethyltocols. Many of the tocopherols demonstrate vitamin E activity. Beta, gamma and delta are stereoisomers of alpha-tocopherol. Esters of tocopherol are often used in cosmetic and personal care products. These esters include, tocopheryl acetate, the acetic acid ester of tocopherol; tocopheryl linoleate, the linoleic acid ester of tocopherol; tocopheryl linoleate/oleate, a mixture of linoleic and oleic acid esters of tocopherol; tocopheryl nicotinate, the nicotinic acid ester of tocopherol; and tocopheryl succinate, the succinic acid ester of tocopherol. Potassium ascorbyl tocopheryl phosphate, a salt of both vitamin E (tocopherol) and vitamin C (ascorbic acid) may also be used in cosmetic products.

Other tocopherol-derived ingredients that may be found in cosmetic products include dioleyl tocopheryl methylsilanol, which is the dioleyl ether of tocopheryl acetate monoether with methylsilanetriol, and tocophersolan, which is also called tocopheryl polyethylene glycol 1000 succinate. The addition of succinic acid and an average of 22 ethylene oxide groups to tocopheryl makes tocophersolan a water-soluble form of tocopherol.

Mannitol is also an exemplary stabilizer due to its low hygroscopicity, excellent chemical and physical drug compatibility, better sweetness and relatively slower dissolution kinetics. It also has relatively low aqueous solubility and good dispersibility and often used to enhance formulation stability where other excipients have failed. Mannitol can be used in a wide array of dosage forms, including but not limited to, tablets, capsules, sachets, pastilles, liquids, emulsions, suspensions, ointments, paste, lotions and intravenous solutions.

Mannitol also serves as a matrix forming additive for lyophilization. When used at concentrations up to 10% w/v, mannitol forms an amorphous (non-crystalline) matrix which supports proteins and other biomolecules for freeze drying. It is generally inert and once freeze dried, rehydrates rapidly. Its amorphous structure while frozen prevents it from disrupting proteins while providing channels for water sublimation during processing.

Similar to mannitol, sucrose is also widely used in tablet form for oral delivery due to its sweetness and palatability. Sucrose, is a non-reducing disaccharide (glucose linked by its anomeric carbon to fructose) that is widely used as a lyoprotectant.

Trehalose ($\alpha$-D-glucopyranosyl $\alpha$-D-glucopyranoside), a disaccharide known for its antioxidant properties, consists of glucoses. Trehalose widely exists in microorganisms, mushrooms, insects, etc., although in relatively low quantities. Trehalose is a non-reducing saccharide, so that it neither reacts with substances containing amino groups such as amino acids and proteins, induces the amino-carbonyl reaction, nor deteriorates amino acid-containing substances. Thus, trehalose can be used without a fear of causing an unsatisfactory browning and deterioration.

Trehalose is also believed to inhibit the inflammatory cascade, thereby suppressing cytokine production. Trehalose is a unique sugar capable of protecting biomolecules against environmental stress and may inhibit the inflammatory cascade that in turn causes oxidative damage and cytokines production. Trehalose has also been shown to preserve cell viability, during exposure to a range of environmental stress, such as heat shock, dehydration and hypoxia.

Trehalose is also a common food additive because it is a strong antioxidant and sweetener, and it is often used as a stabilizing agent in pharmaceutical preparations. Trehalose, like sucrose, is a non-reducing disaccharide (two glucose molecules linked by the anomeric carbon) that can act as an effective lyoprotectant for the freeze drying of proteins and other biomolecules. During the freeze drying process, proteins can denature as water is removed unless a substitute molecule is available to support the structure of the protein. Trehalose fills the void left by exiting water and prevents this denaturation. When used at concentrations as low as 2% it can effectively protect proteins and other biomolecules.

Useful forms of trehalose can include trehalose dihydrate (TD) which is crystalline, amorphous trehalose (AT) which is a vitreous form, and the anhydrous forms of trehalose, anhydrous amorphous trehalose (AAT) and anhydrous crystalline trehalose (ACT). Powdered anhydrous trehalose may contain AAT and/or ACT. The term "trehalose," as used herein, refers to any physical form of trehalose including anhydrous, partially hydrated, fully hydrated and mixtures and solutions thereof. The manufacture and use of anhydrous trehalose from TD can be found in International Publication No.: PCT/GB97/00367, the disclosure of which is incorporated into this specification by reference.

The addition of trehalose to the formulation or composition can help stabilize the other components of the composition as well as inhibit damaging inflammatory cascades. Trehalose can be present in liquid, solid, lyophilized or crystalline forms. When present in liquid form, trehalose can be in a buffered solution. Solvents that can be used to solubilize trehalose can include, but are not limited to, water, saline or other salt solutions, buffer solutions such as phosphate buffered saline, histidine, lactate, succinate, glycine, and glutamate, dextrose, glycerol, as well as combinations thereof. Particularly, trehalose can be present in the formulation as a solution.

At least one stabilizer, can be present in the formulation. Solvents that can be used to solubilize the stabilizer can include, but are not limited to, water, saline or other salt solutions, buffer solutions such as phosphate buffered saline, histidine, lactate, succinate, glycine, and glutamate, dextrose, glycerol, as well as combinations thereof. Particularly, the stabilizer can be present in the formulation as a solution.

The concentration of the at least one stabilizer present in the formulation can vary, but in an exemplary embodiment at least one excipient is provided at a pharmaceutically effective amount. In an exemplary embodiment, the at least one stabilizer has a concentration of at least about 1 mg/mL, at least about 5 mg/mL, at least about 50 mg/mL, at least about 100 mg/mL, or in some embodiments the concentration can be at least about 200 mg/mL. Suitable concentrations of at least one stabilizer can include about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mg, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 70 mg/mL, 80 mg/mL, 90 mg/mL, 100 mg/mL, 110 mg/mL, 120 mg/mL, 130 mg/mL, 140 mg/mL, 150 mg/mL, 160 mg/mL, 160 mg/mL, 170 mg/mL, 180 mg/mL, 190 mg/mL, 200 mg/mL, 300 mg/mL, 400 mg/mL, 500 mg/mL, 600 mg/mL or more or any range derivable therein. Stabilizers can also be in a concentration in a range of about 0.1-60% by weight; about 0.1-50% by weight, about 0.1-45% by weight; or about 0.1-20% by weight. Other suitable concentrations of at least one excipient can include about 0.1%, 0.5%, 1%, 2.5%, 5%, 6%, 7%, 8%, 9% 10%, 11%, 12%, 13%, 14%, 15%, 16%, 17%, 18%, 19%, 20%, 25%, 30%, 35%, 40%, 45%, 50%, 55%, or about 60% by weight.

Lyophilization

Any one or more of the components present in the compositions and methods of the present invention can be lyophilized using various techniques known in the art. Lyophilization is a dehydration process that is typically used to preserve a perishable material, and it works by freezing the material and then reducing the surrounding pressure and adding enough heat to allow the frozen water in the material to sublime directly from the solid phase to the gas phase. Standard lyophilization techniques known in the art can be used to lyophilize any one or more of the components. In an exemplary embodiment, glucosamine and chondroitin sulfate are lyophilized, either together in a mixture, or separately. In another embodiment, the hyaluronic acid is lyophilized. In another embodiment, the glucosamine, chondroitin sulfate and hyaluronic acid are lyophilized, either together in a mixture or separately.

Prior to lyophilization, various solvents can be used to form an aqueous mixture containing the component(s) to be lyophilized. In an exemplary embodiment, the aqueous mixture is prepared by combining water with one or more of the components. The component(s) can be present within the mixture at various amounts, for example in the range of about 0.05 mg/mL to 10 mg/mL rhGDF-5. In an exemplary embodiment, the composition is filter sterilized, such as with a 0.2 μm filter, prior to lyophilization.

In one embodiment, the component(s) can be lyophilized using the following cycle:

Freezing: from ambient temperature to 5° C. in 15 minutes
  Hold at 5° C. for 100 minutes
  Down to −45° C. in 50 minutes
  Hold at −45° C. for 180 minutes
  Primary Drying: set pressure at 50 mTorr
  Shelf Up to −15° C. in 175 minutes
  Hold at −15° C. for 2300 minutes
  Secondary Drying: set pressure at 75 mTorr
  Shelf Up to 25° C. in 200 minutes
  Hold for 900 minutes
  Cycle end: backfill with nitrogen to −730 Torr
  Capping and crimping Variations to the temperatures, times and settings can be made in accordance to practices used by a person of skilled in the art. Variations may include, but are not limited to, cycling temperatures for the freezing cycle, drying temperatures and end cycles. Variations may also include differences in holding times for the freezing, drying and capping/crimping cycles. Variations may also include differences in set pressures for the drying cycles and capping/crimping cycles. In addition, the number of drying cycles may be increased or decreased depending on the machine used or component(s) to be lyophilized.

The addition of a buffering agent can provide for improved solubility and stability of the compounds in lyophilized formulations. Biocompatible buffering agents known in the art can be used, such as glycine; sodium, potassium, or calcium salts of acetate; sodium, potassium, or calcium salts of citrate; sodium, potassium, or calcium salts of lactate; sodium or potassium salts of phosphate, including mono-basic phosphate, di-basic phosphate, tri-basic phosphate and mixtures thereof. The buffering agents can additionally have sugar added to the composition to function as a bulking agent. The pH typically can be controlled within about 2.0 to about 5.0 pH units, and more typically within about 2.5 to about 3.5 pH units.

Formulations

While HA alone can be effective to treat joint conditions, the compositions and formulations described herein provide an improved approach for treating joint conditions.

It is well known in the art that most of the available injectable formulations in the market are isotonic. The pH of the available formulations is either close to the pH of synovial fluid (i.e., pH 7.4) or slightly lower, but not below pH ~5.5, to allow for optimum stability of the active ingredient, while minimizing possible side effects of non-physiological pH values, such as pain or tissue damage at the injection site. However, the acidic compositions and formulations with high osmolality described herein surprisingly produced unexpected benefits. The disclosed compositions and formulations demonstrated improved efficacy in pain relief and disease modification for treating joint conditions. Further, compositions and formulations did not cause any side effects (such as pain, inflammation or tissue damage at the injection site) that one would have expected for a low pH and/or a high osmolality IA formulation based on the current knowledge. The acidic compositions and formulations also provide an excellent preserved solution against the contaminating action of microorganisms such as bacteria and fungi. Such a preserved solution not only provides an excellent sterile environment, but also makes it easier to produce a commercial kit with longer shelf-life.

In addition, the combination of HA, glucosamine and chondroitin sulfate also addresses the issue of low bioavailability in the arthritic joint from the oral administration of glucosamine and chondroitin sulfate. As shown in the data and examples provided herein, both very low dose of glucosamine and chondroitin sulfate and high dose of glucosamine and chondroitin sulfate can provide equal efficacy in pain relief and disease modification during the treatment.

Accordingly, provided herein is a composition that includes an injectable formulation encompassing HA, glucosamine, and/or chondroitin sulfate.

The concentration of HA present in the formulations can vary, but in an exemplary embodiment HA is provided at a pharmaceutically effective amount. Suitable concentrations of HA include about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mg, 12.5 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/1, 60 mg/mL or more or any range derivable therein. In some embodiments, the HA can have a concentration in the range of about 3.6 mg/mL to about 36 mg/mL.

The concentration of the GlcN used in the formulations can also vary. In some embodiments, a high dose of GlcN (e.g., about 180 mg/mL, about 170 mg/mL, about 160 mg/mL, about 150 mg/mL, about 140 mg/mL, about 130 mg/mL, about 120 mg/mL, about 110 mg/mL, about 100 mg/mL, about 90 mg/mL, about 80 mg/mL, about 70 mg/mL, about 60 mg/mL, about 50 mg/mL, about 40 mg/mL, about 38 mg/mL, about 36 mg/mL, about 34 mg/mL, about 32 mg/mL, 30 mg/mL, 28 mg/mL, 25 mg/mL, 22 mg/mL, 20 mg/mL, about 19 mg/mL, about 18.5 mg/mL, about 18 mg/mL) per injection is used. In some embodiments, a low dose of GlcN (e.g., about 5.0 mg/mL, about 2.5 mg/mL, about 2.0 mg/mL, about 1.8 mg/mL, about 1.5 mg/mL, about 1.0 mg/mL, about 0.5 mg/mL, about 0.018 mg/mL, about 0.0018 mg/mL, about 0.00018 mg/mL or lower) per injection is used.

CS can be used in the formulations described herein at various concentrations. In an exemplary embodiment CS is provided at a pharmaceutically effective amount. In some embodiments, a high dose of CS (e.g., about 80 mg/mL, about 75 mg/mL, about 70 mg/mL, about 65 mg/mL, about 60 mg/mL, about 55 mg/mL, about 50 mg/mL, about 45 mg/mL, about 40 mg/mL, about 38 mg/mL, about 36 mg/mL, about 34 mg/mL, about 32 mg/mL, 30 mg/mL, 28 mg/mL, 25 mg/mL, 22 mg/mL, 20 mg/mL, about 19 mg/mL, about 18.5 mg/mL, about 18 mg/mL) per injection is used. In some embodiments, a low dose of CS (e.g., about 5.0 mg/mL, about 2.5 mg/mL, about 2.0 mg/mL, about 1.8 mg/mL, about 1.5 mg/mL, about 1.0 mg/mL, about 0.5 mg/mL, about 0.018 mg/mL, about 0.1 mg/mL, about 0.05 mg/mL, about 0.005 mg/mL or lower) per injection is used.

In some embodiments, the formulations disclosed herein include a pharmaceutically effective amount of HA, a high concentration/dose of GlcN (e.g., about 180 mg/mL, about 170 mg/mL, about 160 mg/mL, about 150 mg/mL, about 140 mg/mL, about 130 mg/mL, about 120 mg/mL, about 110 mg/mL, about 100 mg/mL, about 90 mg/mL, about 80 mg/mL, about 70 mg/mL, about 60 mg/mL, about 50 mg/mL, about 40 mg/mL, about 38 mg/mL, about 36 mg/mL, about 34 mg/mL, about 32 mg/mL, 30 mg/mL, 28 mg/mL, 25 mg/mL, 22 mg/mL, 20 mg/mL, about 19 mg/mL, about 18.5 mg/mL, about 18 mg/mL), and a high concentration/dose of CS (e.g., about 80 mg/mL, about 75 mg/mL, about 70 mg/mL, about 65 mg/mL, about 60 mg/mL, about 55 mg/mL, about 50 mg/mL, about 45 mg/mL, about 40 mg/mL, about 38 mg/mL, about 36 mg/mL, about 34 mg/mL, about 32 mg/mL, 30 mg/mL, 28 mg/mL, 25 mg/mL, 22 mg/mL, 20 mg/mL, about 19 mg/mL, about 18.5 mg/mL, about 18 mg/mL).

In some embodiments, the formulations disclosed herein include a pharmaceutically effective amount of HA and a high concentration/dose of CS (e.g., about 80 mg/mL, about 75 mg/mL, about 70 mg/mL, about 65 mg/mL, about 60 mg/mL, about 55 mg/mL, about 50 mg/mL, about 45 mg/mL, about 40 mg/mL, about 38 mg/mL, about 36 mg/mL, about 34 mg/mL, about 32 mg/mL, 30 mg/mL, 28 mg/mL, 25 mg/mL, 22 mg/mL, 20 mg/mL, about 19 mg/mL, about 18.5 mg/mL, about 18 mg/mL).

In some embodiments, the formulations disclosed herein include a pharmaceutically effective amount of HA, a low concentration/dose of GlcN (e.g., about 5.0 mg/mL, about 2.5 mg/mL, about 2.0 mg/mL, about 1.8 mg/mL, about 1.5 mg/mL, about 1.0 mg/mL, about 0.5 mg/mL, about 0.018 mg/mL about 0.0018 mg/mL, about 0.00018 mg/mL or lower), and a low concentration/dose of CS (e.g., about 5.0 mg/mL, about 2.5 mg/mL, about 2.0 mg/mL, about 1.8 mg/mL, about 1.5 mg/mL, about 1.0 mg/mL, about 0.5 mg/mL, about 0.018 mg/mL, about 0.1 mg/mL, about 0.05 mg/mL, about 0.005 mg/mL or lower).

In some embodiments, the formulations disclosed herein include a pharmaceutically effective amount of HA and a low concentration/dose of CS (e.g., about 5.0 mg/mL, about 2.5 mg/mL, about 2.0 mg/mL, about 1.8 mg/mL, about 1.5 mg/mL, about 1.0 mg/mL, about 0.5 mg/mL, about 0.018 mg/mL, about 0.1 mg/mL, about 0.05 mg/mL, about 0.005 mg/mL or lower).

It is desirable that the formulations described herein have a pH of about 3.0 to about 5.0. For example, the formulation has a pH value of about 3.0 to about 4.0, about 3.5 to about 4.5 or about 3.5 to about 5.0. For example, the formulation has a pH value of about 3.0, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 50. Typically, the formulation has a pH value of about 3.5 to about 4.0.

The compositions and formulations can be used in a method of treating a joint by administering the composition or the formulation to a subject, such as by injection into the body of the subject (e.g., by injection into a joint) as discussed below. The results after injecting the acidic and high osmolality composition are surprisingly good with no evidence of post injection pain or tissue degradation.

In one aspect, a composition for treating a joint condition is disclosed. The composition includes a solution of hyaluronic acid (HA) combined with glucosamine (GlcN) and chondroitin sulfate (CS). In the composition, all or some of the components can be liquid, solid, or lyophilized. In an exemplary embodiment, a composition of GlcN/CS is lyophilized and combined with liquid HA.

The compositions can be in a variety of forms. These include, for example, liquid, semi-solid and solid dosage forms, such as liquid solutions (e.g., injectable and infusible solutions), dispersions or suspensions, tablets, pills, and powders. The form ultimately used depends on the intended mode of administration and therapeutic application. Typical compositions are in the form of injectable or infusible solutions, such as compositions similar to those used for in vivo injection. One useful mode of administration is parenteral (e.g., intra-articular, subcutaneous, intraperitoneal, intramuscular). In one embodiment, the composition is administered by infusion or injection directly into the target area, such as a joint. In another embodiment, the composition can be administered by intramuscular or subcutaneous injection.

In an exemplary embodiment, the components are configured to be combined intraoperatively, i.e., immediately before or during an operation. In one embodiment, the components are combined about 60 minutes or less before injection. In another embodiment, the components are combined about 30 minutes or less prior to injection. The components, when combined, can form a resulting composition having each component present in the composition at various amounts. The amount of each component in the composition can vary.

In one embodiment, solvents can be included in the composition. Solvents that can be used to solubilize one or more of the components include, for example, water, acidic solvents, hydrochloric acid, acetic acid, benzoic acid, phosphate buffered saline, dextrose, glycerol, ethanol and the like, as well as combinations thereof. Solvents that can be used to solubilize HA can include, but are not limited to, water, saline or other salt solutions, buffer solutions such as phosphate buffered saline, histidine, lactate, succinate, glycine and glutamate, dextrose, glycerol, and other suitable solvents, as well as combinations thereof. Solvents that can be used to solubilize the GlcN/CS can include water, saline, phosphate-buffered saline, hydrochloric acid, acetic acid, benzoic acid, acidic solvent, and other solvents suitable for solubilization of this solution. The compositions can also include additional components, such as stabilizers, buffers, isotonic agents, or other joint treatment components.

Concentration of the components can affect the pH and osmolality of the resulting composition. For example, in some embodiments, lower concentrations of glucosamine and chondroitin sulfate may be used to avoid a composition being too acidic (such as a pH lower than 2.0). Table 1 lists pH values of exemplary compositions with various concentrations of each component. For this composition, GlcN is in the form of GlcN-HCl salt.

TABLE 1 pH of exemplary compositions varied by concentration

| Composition | pH |
|---|---|
| Orthovisc ® (high molecular weight hyaluronan) | 5.78 |
| Saline (0.9% sodium chloride) | 6.80 |
| Orthovisc ® (high molecular weight hyaluronan) and 20 mg/mL CS and GlcN | 3.75 |
| Orthovisc ® (high molecular weight hyaluronan) and 2 mg/mL CS and GlcN | 4.58 |
| Orthovisc ® (high molecular weight hyaluronan) and 0.2 mg/mL CS and GlcN | 5.33 |

*The samples used in measuring pH were mixed, lyophilized, and stored at 4° C. The pH of these samples were determined using a Beckman Φ 250 pH meter. A 3-point calibration was performed at 1.68, 4.0, and 7.0.

A person skilled in the art will appreciate that the concentrations of each component can be modified to regulate pH and/or the therapeutic outcome. In an exemplary embodiment the concentration of glucosamine can be about 0.005-54, 1.8, 1.8-18, 2.0, 2.0-20, 18, 20, 2.0-40, 20-30, 10-40, or 40 mg/mL. In another embodiment, the concentration of chondroitin sulfate can be about 0.005-54, 1.8, 1.8-18, 2.0, 2.0-20, 18, 20, 2.0-40, 20-30, 10-40, or 40 mg/mL. In another embodiment the concentration of HA can be about 3.6-36, 10-20, 12, 15, or 12-17.5 mg/mL. In yet another embodiment the concentration of glucosamine can be a high concentration, such as in the range of about 18-20 mg/mL, the concentration of chondroitin sulfate can be a high concentration, such as in the range of about 18-20 mg/mL, and the concentration of HA can be in the range of about 12-17.5 mg/mL. In yet another embodiment, the weight ratio of glucosamine to chondroitin sulfate is about 1:1, although other ratios are possible (such as any ratio between about 0.445 to about 444,445).

In one embodiment, the composition can have a concentration having any component concentrations within the ranges listed above. In one embodiment, the resultant composition can have a pH of at least about 3, in the range of about 3 to 8, in the range of about 3 to 5, or typically in the range of about 3 to 4. Further, the composition can have an osmolality in the range of about 300 to 3,000 mOSM (e.g., about 300, about 350, about 400, about 450, about 500, about 600, about 650, about 700, about 750, about 800, about 850, about 900, about 950, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900 or about 3000 mOSM). In some embodiments, composition can have an osmolality in the range of about 300 to 700 mOSM, in the range of about 350-600 mOSM, or typically in the range of 400-600 mOSM.

The compositions can be incorporated into pharmaceutical compositions suitable for administration to a subject. Typically, the pharmaceutical composition comprises HA and at least one of GlcN or CS and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, hydrochloric acid, acetic acid, benzoic acid, acidic solvent, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the composition.

The components and/or the resulting composition can be sterilized prior to use using various techniques known in the art. Sterile injectable compositions can be prepared by incorporating the active compound(s) in a therapeutically effective or beneficial amount in an appropriate solvent with one or a combination of ingredients, as required, followed by filtered sterilization. Generally, dispersions are prepared by incorporating a compound(s), such as HA into a sterile vehicle which contains a basic dispersion medium and any required other ingredients. In the case of sterile powders for the preparation of sterile injectable compositions, some methods can include preparation of vacuum dried and freeze-dried components which yield a powder of the composition plus any additional desired ingredients from a previously sterile-filtered composition thereof.

Sterile injectable solutions can be prepared by incorporating the active compound in a therapeutically effective or beneficial amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The volume for each injection may vary according to the size of the joint where the injection occurs. Suitable volume for each injection can be about 0.5 mL to about 10 mL (e.g., about 0.5 mL, about 1.0 mL, about 1.5 mL, about 2 mL, about 2.5 mL, about 3 mL, about 3.5 mL, about 4 mL, about 4.5 mL, about 5 mL, about 5.5 mL, about 6 mL, about 6.5 mL, about 7 mL, about 7.5 mL, about 8 mL, about 8.5 mL, about 9 mL, about 9.5 mL or about 10 mL). In some embodiments, the volume of a single injection for knee, shoulder and hip can be in the range of about 1 ml to about 10 ml. In some embodiments, the volume of a single injection for hand can be in the range of about 500 µl to about 1.5 ml.

Administration/Method

The compositions of this invention can be administered, for in vivo applications, parenterally by injection or by gradual perfusion over time. Administration may be intra-articular, intravenous, intraperitoneal, intramuscular, subcutaneous, intracavity, or transdermal.

Examples of symptoms or diseases, for which the composition and methods disclosed herein can be useful, encompass treating articular disorders, such as arthritis caused by infections, injuries, allergies, metabolic disorders, etc., rheumatoids such as chronic rheumatoid arthritis, and systemic lupus erythematosus; articular disorders accompanied by gout, arthropathy such as osteoarthritis, internal derangement, hydrarthrosis, stiff neck, lumbago, etc. Varying the effects depending on the use of the composition or the types of diseases to be treated, the agent can exert desired prophylactic and alleviative effects, or even therapeutic effects on swelling, pain, inflammation, and destroying of articulations without seriously affecting living bodies. The composition for treating articular disorder can be used to prevent the onset of articulation disorders, as well as to improve, alleviate, and cure the symptoms after their onsets.

The methods of treatment can include directly injecting the compositions into the target area, such as a joint. Injections can be performed as often as daily, weekly, several times a week, bi monthly, several times a month, monthly, or as often as needed as to provide relief of symptoms. In alternative embodiments, the compositions of the invention may be administered intermittently over a period of months. It will be appreciated that administration regimens may be continued for extended periods (e.g., on the order of years) to maintain beneficial therapeutic effects provided by initial treatments. In yet other embodiments, maintenance therapy may be effected following an acute dosing regimen designed to reduce the immediate symptoms of the joint condition, such as osteoarthritis. In most embodiments, however, the compositions of the invention are administered to the patient according to the methods described herein at least until the symptoms of the joint condition, such as OA, are alleviated or reduced. More commonly, the compositions of the invention and methods of the invention are used for a period of time after the symptoms are reduced to a tolerable level or completely eliminated so as to result in an improvement in the physiological structure of the joint by reducing or eliminating the underlying physiological causes of the joint condition.

For intra-articular use, from about 1 to about 30 mg/mL of HA and about 0.018 to about 30 mg/mL of GlcN/CS per joint, depending on the size of the joint and severity of the condition, can be injected. The frequency of subsequent injections into a given joint are spaced to the time of recurrence of symptoms in the joint. Illustratively, dosage levels in humans of the composition can be: knee, about 1 to about 30 mg/mL HA and 0.018 to about 20 mg/mL of GlcN/CS per joint injection; shoulder, about 1 to about 30 mg/mL of HA 0.018 to about 20 mg/mL of GlcN/CS per joint injection; metacarpal or proximal intraphalangeal, about 1 mg/mL to about 30 mg/mL of HA and 0.018 to about 20 mg/mL of GlcN/CS per joint injection; and elbow, about 1 to about 30 mg/mL of HA and 0.018 to about 20 mg/mL of GlcN/CS per joint injection. In some embodiments, the total amount of injection can range from about 1 mg/mL to about 200 mg/mL of HA, about 0.005 mg/mL to about 150 mg/mL of GlcN, and about 0.005 mg/mL to about 150 mg/mL of CS.

It will be understood, however, that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy. The pharmaceutical compositions can be prepared and administered in dose units. Under certain circumstances, however, higher or lower dose units may be appropriate. The administration of the dose unit can be carried out both by single administration of the composition or administration can be performed in several smaller dose units and also by multiple administrations of subdivided doses at specific intervals.

In one embodiment, the HA and glucosamine and chondroitin sulfate can be configured to be combined and administered intra-articularly as part of a surgical procedure involving an articulating joint, either immediately before, during, or immediately after the surgical procedure. The HA and GlcN/CS can be co-administered or simultaneously administered in the same formulation or in two different formulations that are combined via the same route. GlcN is not stable at a low pH and will degrade with time, accordingly it is not desirable to have a formulation including GlcN at a low pH. In a preferred embodiment, the HA and GlcN/CS components can be combined just prior to administration of the HA and GlcN/CS. The combination can occur within seconds, minutes, hours, days or weeks prior to the administration of the composition. In another embodiment it is preferred to combine GlcN and chondroitin sulfate, either in a mixture or separately, with HA less than about 60 minutes (e.g., about 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5 minutes) prior to injection. In a typical embodiment, the combination occurs about 30 minutes or less before administration. In some embodiments, the combination occurs about 15 minutes or less before administration. In some embodiments, the combination occurs about 5 minutes or less before administration.

In one embodiment, the medical condition is osteoarthritis (OA) and the composition is administered in a joint space, such as, for example, a knee, shoulder, temporomandibular and carpometacarpal joints, elbow, hip, wrist, ankle, and lumbar zygapophysial (facet) joints in the spine. The viscosupplementation may be accomplished via a single injection or multiple intra-articular injections administered over a period of weeks into the knee or other afflicted joints. For example, a human subject with knee OA may receive one, two, or three injections of about 0.5, 1, 1.5, 2, 3, 4, 5, 6, 7, 8, 9, 10 mL or more per knee. One skilled in the art will appreciate that for other joints, the administered volume can be adjusted, based on the size on the joint.

Kit

The methods and compositions encompass kits for treating articular disorders, such as joints. In yet another aspect, a kit is disclosed. The kit can include a first component being a solution of hyaluronic acid (HA), a second component including an amount of glucosamine and chondroitin (GlcN/CS), and a syringe for injecting a mixture of the first component and the second component. Moreover, the syringe can have a first chamber containing the first component, a second container containing the second component and a plunger configured to inject the second component into the first chamber to mix the first and second components.

The kit can be stored at room temperature. Additionally, the kit can include a syringe containing the HA solution in a single chamber, and the GlcN/CS in a second chamber. The components can be present in liquid, solid or lyophilized form. The kit can further include a diluent, such as water, saline, and a buffer, to solubilize one of the components.

The components can be stored separately to increase shelf-life. The individual components can be lyophilized or in solid form in one syringe/cartridge with diluent or a second component in a second syringe/cartridge. In one embodiment, one of the compounds is in lyophilized form or in solid form and the second compound is a solution capable of combining with the lyophilized/solid compound.

Pre-filled dual-chamber syringes and/or cartridges can also be utilized with the components and compositions. Pre-filled dual-chamber syringes enable the sequential administration of two separate compositions with a single syringe push, thereby replacing two syringes with one. The benefits of a single delivery capability include increasing the speed and ease of drug administration; reducing risk of infection by reducing the number of connections; lowering the risk of drug administration or sequence errors, and quicker delivery of compositions requiring combination prior to administration. The dual-chamber syringe can accommodate lyophilized, powder or liquid formulations in the front chamber combined with diluents, saline or buffer in the rear chamber.

FIG. 1 illustrates one embodiment of a mixing and delivery system that is in the form of a dual chamber syringe 10. As shown, the dual chamber syringe 10 generally includes a housing having proximal and distal chambers 14, 12 separated by a valve 16. A plunger 18 is slidably disposed within the proximal chamber 14 and is configured to inject fluid present within the proximal chamber 14 into the distal chamber 12 to thereby mix the components. In one embodiment, the first component, e.g., liquid HA with at least one stabilizer, can be present in the proximal chamber 14 and an additional component, e.g., one or more additional components, can be present in the distal chamber 12. Alternatively, the first component, e.g., liquid HA, can be present in the proximal chamber 14 with at least one stabilizer, such as trehalose, and at least one additional component, e.g., chondroitin sulfate, can be present in the distal chamber 12. The plunger 18 can be advanced through the proximal chamber 14 to inject the first component, e.g., liquid HA with at least one stabilizer, into the distal chamber 12 containing the second component, e.g., one or more additional components. In another embodiment, the proximal chamber 14 can contain a solvent, such as water or saline, and the distal chamber 12 can contain all of the components in solid form. For example, the distal chamber 12 can contain lyophilized or solid HA with at least one stabilizer. The plunger 18 can be advanced through the proximal chamber 14 to inject the solvent into the distal chamber 12, thereby solubilizing the components in the distal chamber 12. Once all components are combined in the distal chamber 12, the composition can be delivered to tissue, for example by attaching a needle to the distal end of the dual chamber syringe.

Figure 2:
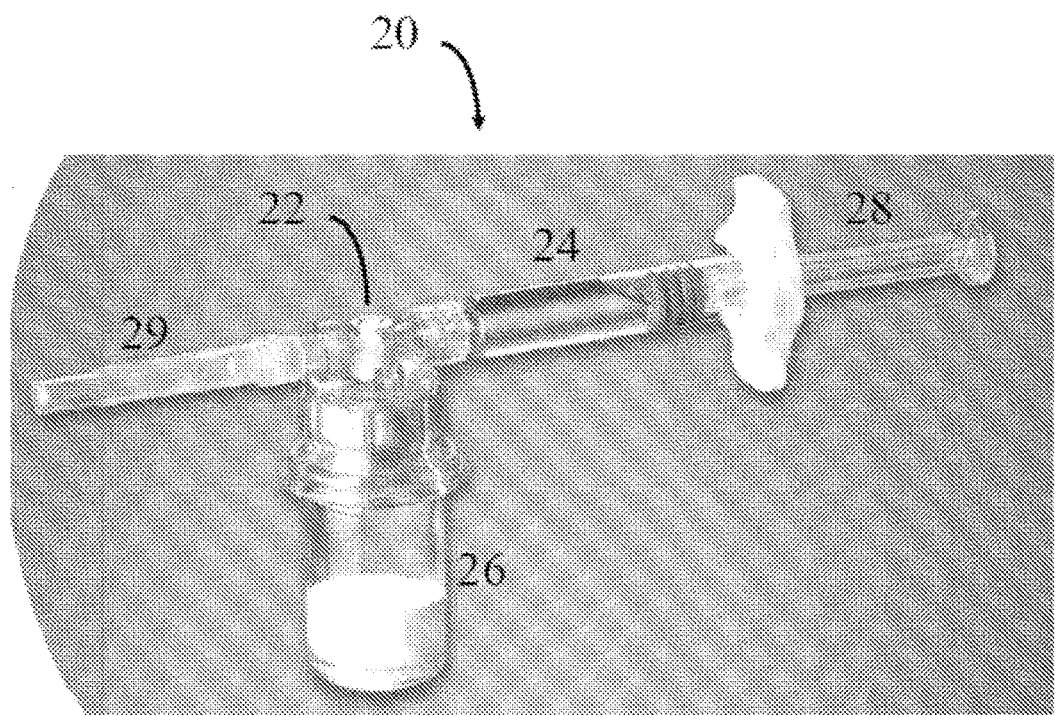
FIG. 2 is a perspective view of another embodiment of a mixing and delivery system for use with the present compositions and methods.

FIG. 2 illustrates another embodiment of a mixing and delivery system 20, which is sold commercially under the trade name MixJect®. In this embodiment, the system includes a fluid control assembly 22 that is coupled between a syringe 24 and a vial 26. The syringe 24 defines a first chamber which can contain a liquid, such as liquid HA or a solvent, and the vial defines a second chamber which can contain a solid, such as one or more additional components. Deployment of the plunger 28 through the syringe 24 will inject the liquid through the control system and into the vial 26, where the solid will be solubilized by the liquid. Once the components are fully solubilized, the vial 26 can be inverted and the plunger 28 can be retracted to draw the composition back into the first chamber in the syringe 24. The vial 26 can then be removed from the system, and the composition can be injected from the syringe through a needle 29 and into tissue.

A person skilled in the art will appreciate that any dual chamber systems known in the art can be used, and that the chambers can be side-by-side chambers with separate syringe plungers that mix into a single chamber or linear chambers with a single plunger.

Prefilled syringes can contain the exact deliverable dose of desired compounds and diluents. The prefilled syringes can contain volumes from about 0.1 mL, 0.2 mL, 0.3 mL, 0.4 mL, 0.5 mL, 0.6 mL, 0.7 mL, 0.8 mL, 0.9 mL, 1.0 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL, 8 mL, 8.5 mL, 9 mL, 9.5 mL, 10 mL or more or any derivative therein. The volume for injection can vary based on the size of the joint for delivery. The volume of composition used can be varied based on the type of administration including the joint to which it is being administered, and the frequency of administration. One skilled in the art will appreciate that the volume for injection can be varied and optimized based on many other factors.

The dual syringe and/or cartridge can be side-by-side chambers with separate syringe plungers that mix into a single chamber or linear chambers with one plunger. The dual chamber syringe and/or cartridges can also have a stopper or connector in the middle to serve as a barrier between the two chambers. The stopper or connector can be removed to allow mixing or combining of the compounds in the two chambers.

A person skilled in the art will appreciate that any dual chamber systems known in the art can be used, and that the chambers can be side-by-side chambers with separate syringe plungers that mix into a single chamber or linear chambers with a single plunger.

EXPERIMENTAL DATA

Example 1: Liquid/Liquid Formulation

A stock solution of GlcN/CS was prepared containing 8.7 mg/mL of glucosamine (as the hydrochloride salt) and 8.7 mg/mL of chondroitin sulfate. Just prior to intra-articular injection, approximately 103 uL of this stock was combined with 400 uL of Orthovisc® (high molecular weight hyaluronan) having an HA concentration of 15 mg/mL. Inter-syringe mixing of the two solutions was carried out using a three-way stopcock. The resultant solution contained 12 mg/mL HA, 1.8 mg/mL GlcN, and 1.8 mg/mL CS. The solution was aliquoted into smaller syringes for intra-articular injection. Injected volumes were about 50 uL for rat studies.

Example 2: Liquid/Solid Formulation 4 mg of GlcN and 4 mg of CS were lyophilized in a sterile vial. Just prior to injection, 2 mL or 15 mg/mL HA was injected into the lyophilized powder vial and vortexed until complete mixing was achieved. The resultant solution contained 15 mg/mL HA, 2 mg/mL CS and 2 mg/mL GlcN. The solution was aliquoted into smaller syringes for intra-articular injection.

Test Data: Rat MMT Model of Osteoarthritis

Several intra-articular HA/GlcN/CS formulations were tested in the rat medial meniscal tear (MMT) model. In this model, transaction of the medial meniscus results in joint deterioration and reduced weight bearing that mimic human osteoarthritis. This degeneration process occurs over a period of several weeks, with significant degeneration evident at 21 days.

The extent of joint deterioration, as determined primarily by the extent of cartilage lesions formed, is measured using a semi-quantitative histological scoring system. Weight bearing is measured using a commercially available incapacitance apparatus. Weight bearing improvement was determined by area under the curve (AUC) analysis of weekly weight bearing data. This provides a measure of the cumulative effect of the treatment on pain over the course of the experiment.

Beginning one week after MMT surgery, intra-articular injections were given weekly for five weeks, followed by euthanasia at week six. Weight bearing measurements were taken weekly just prior to injection.

HA/GlcN/CS formulations tested in the rat MMT model had the following concentrations:

HA/GlcN/CS=12 mg/mL/0.18 mg/mL/0.18 mg/mL ("the 0.18 mg/mL HA/GlcN/CS group/formulation")

HA/GlcN/CS=12 mg/mL/1.8 mg/mL/1.8 mg/mL ("the 1.8 mg/mL HA/GlcN/CS group/formulation")

HA/GlcN/CS=12 mg/mL/18.0 mg/mL/18.0 mg/mL ("the 18.0 mg/mL HA/GlcN/CS group/formulation")

HA/CS=12 mg/mL/0.18 mg/mL ("the 0.18 mg/mL HA/CS group/formulation")

HA/CS=12 mg/mL/1.8 mg/mL ("the 1.8 mg/mL HA/CS group/formulation")

HA/CS=12 mg/mL/18.0 mg/mL ("the 18 mg/mL HA/CS group/formulation")

HA=12 mg/mL

Untreated Controls

As such, the concentration of HA was held constant at a level that approximates commercially available viscosupplements, while the concentration of glucosamine and chondroitin sulfate was varied. For the present discussion, the 0.18, 1.8, and 18.0 mg/mL designations refer to those concentrations of GlcN and CS in combination with HA. The HA used in the formulations had a molecular weight range specification of 1.0-2.9 million Daltons.

Figure 3:
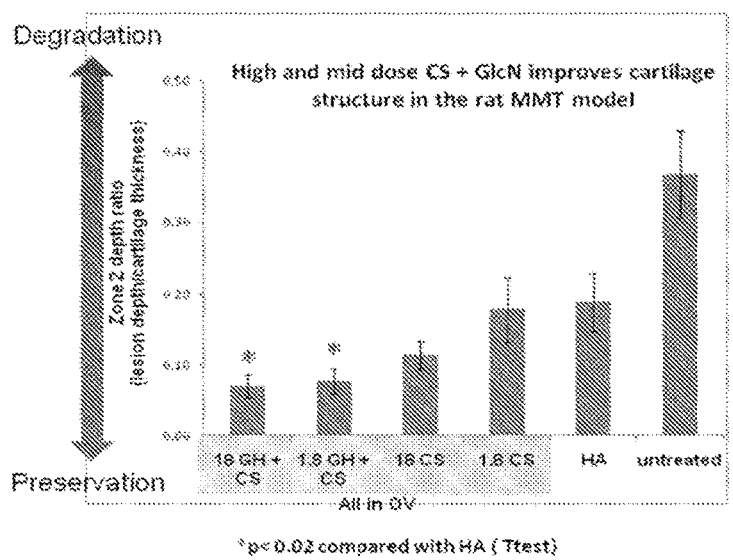
FIG. 3 shows Zone 2 depth ratio (lesion depth/cartilage thickness) results following administration of different compositions in a rat (medial meniscal tear) MMT model.

Histology results, provided in FIG. 3 showed that the 1.8 mg/mL and 18.0 mg/mL HA/GlcN/CS groups gave significant improvement over HA and untreated controls in Zone 2 Depth Ratio, that is, the depth of cartilage lesions in the central ⅓ of the medial compartment of the knee joint. GlcN is also labeled as "GH" in the figures. "OV" used in the figures refers to Orthovisc® (high molecular weight hyaluronan) that contains HA. Thus "OV" is equivalent to "HA" in the figures.

Figure 4:
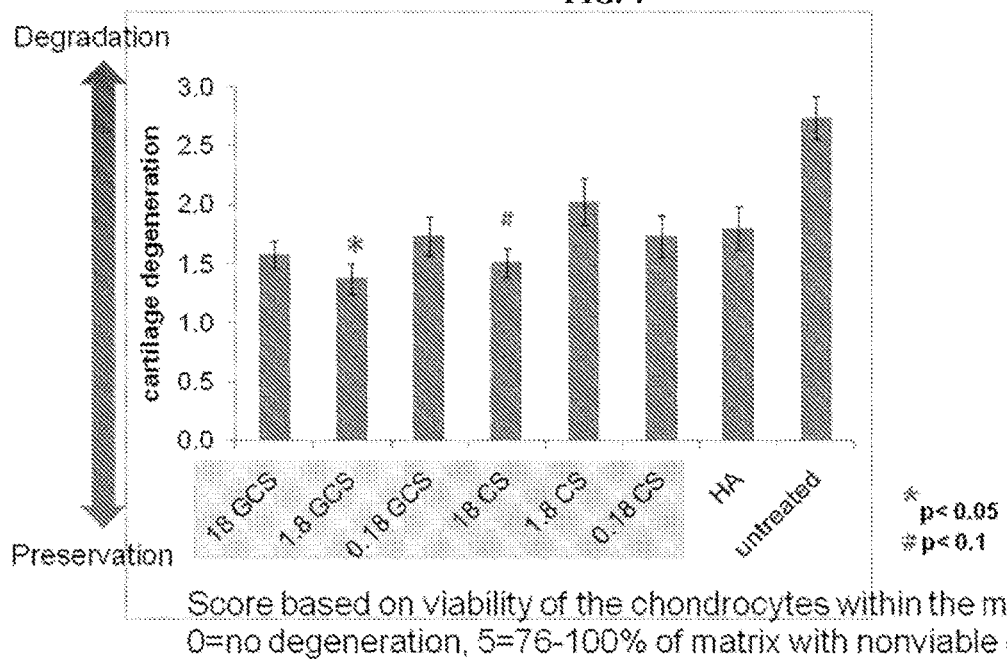
FIG. 4 shows cartilage degeneration score results following administration of different compositions in a rat MMT model.

In another measure of cartilage preservation, the 1.8 mg/mL HA/GlcN/CS ("1.8 GCS") and 18 mg/mL HA/CS ("18 CS") groups showed improvement in cartilage degeneration score as shown in FIG. 4. This is demonstrative of the cellular viability of the remaining cartilage. "GCS" used in this figure means GlcN+CS. OV was used in all three GCS and all three CS groups.

Figure 5:
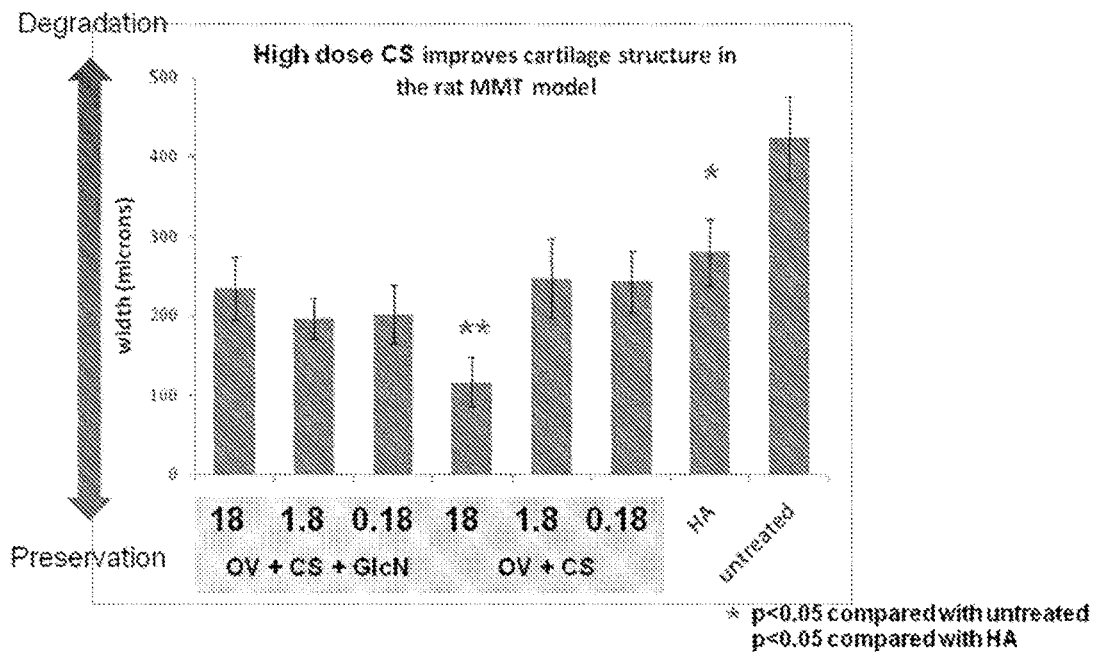
FIG. 5 shows width of lesions as measured by cartilage depletion following administration of different compositions in a rat MMT model.

A further measure of cartilage preservation is the width of lesions as measured by cartilage depletion. FIG. 5 shows the 18 mg/mL HA/CS group showed significant reduction in lesion width compared to HA alone; and that the 18 mg/mL HA/GlcN/CS group also showed significant reduction in lesion width compared to HA alone.

Figure 6:
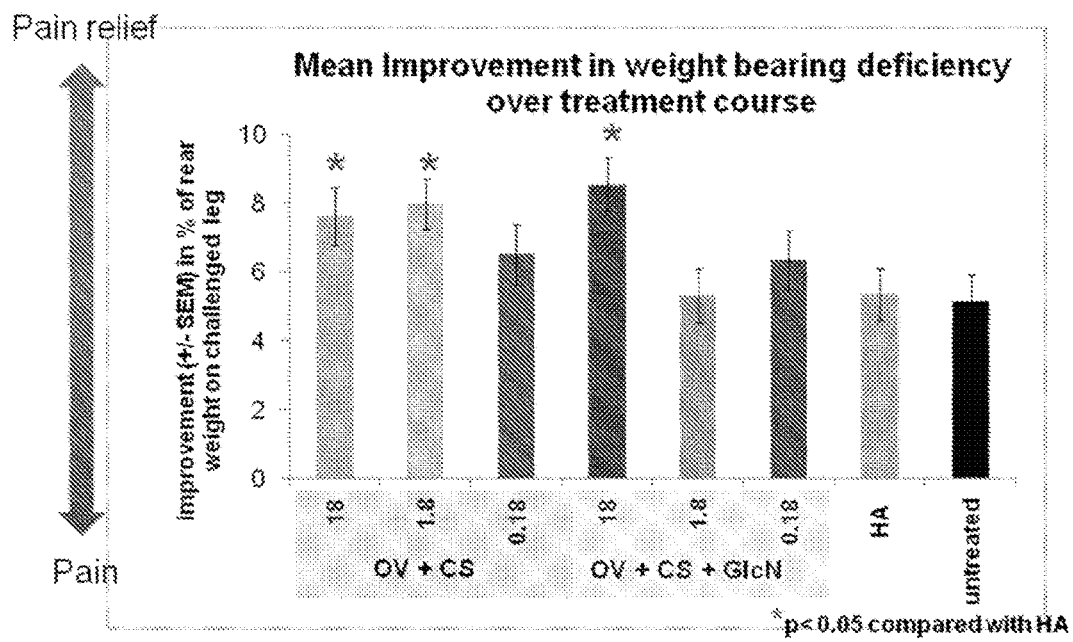
FIG. 6 shows a weight bearing area under the curve (AUC) analysis of weight bearing percentage following administration of different compositions in a rat MMT model.

FIG. 6 shows a weight bearing area under the curve analysis tested in the rat MMT model. The weight bearing area under the curve analysis shows that the 18.0 mg/mL HA/GlcN/CS group gave significant pain relief compared to HA alone. The 18 and 1.8 mg/mL HA/CS groups also gave significant weight bearing improvement.

CFA Model of Inflammatory Arthritis

Because OA is now known to have an inflammatory component, an animal model that mimics inflammatory arthritis was used to test HA/GlcN/CS formulations. Complete Freund's Adjuvant (CFA) comprises an emulsion of killed bacterial cells that is injected systemically or into the joint of a rat to induce severe inflammation. Two CFA studies were conducted, the first using a 200 uL injection of CFA to induce inflammation (CFA #1), the second using an injection volume of 100 uL (CFA #2). Test articles were prepared using the liquid/liquid formulation method described above.

Figure 7:
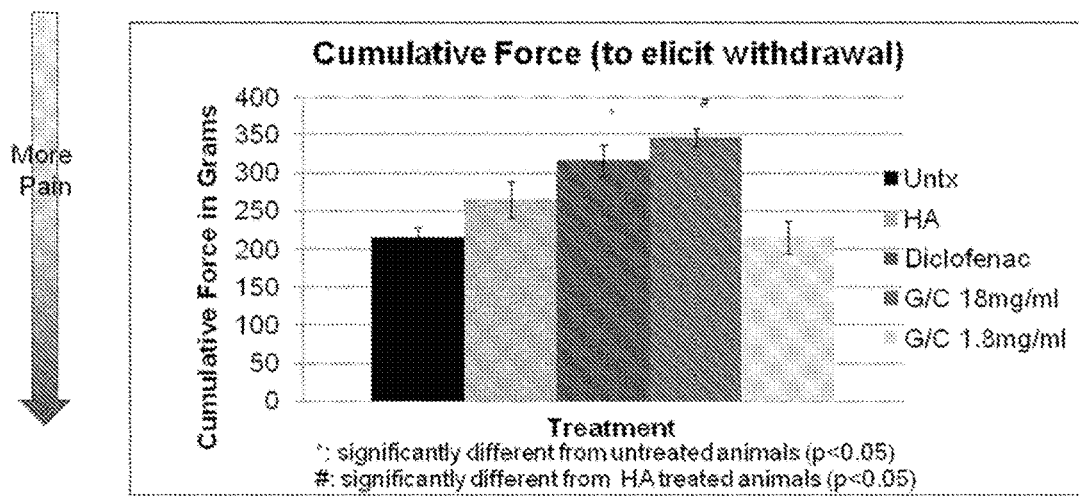
FIG. 7 shows results of an AUC analysis of cumulative force on effected leg in a complete Freund's adjuvant (FCA) model of inflammatory arthritis.

In CFA #1, a single injection of HA/GlcN/CS was given on the fifth day following intra-articular CFA injection, which was sufficient time for the animals to develop substantial inflammation and pain sensitivity. Von Frey filaments were used to assess mechano-allodynia (pain sensation from a normally non-painful stimulus) on days 6, 7, 8, 17, and 21 following CFA injection. The potent NSAID diclofenac was used as a positive control, using a daily oral dose regimen. This protocol was used to test the 18.0 and 1.8 mg/mL HA/GlcN/CS formulations. As with the rat MMT model, the cumulative improvements in pain relief were calculated. As shown in FIG. 7, results of the AUC analysis showed significant improvement in pain relief in the HA, diclofenac and 18 mg/mL HA/GlcN/CS groups. Diclofenac and 18 mg/mL HA/GlcN/CS were also statistically superior to HA alone. Notably, several animals in the diclofenac group died prematurely, indicating that the 18 mg/mL HA/GlcN/CS group had a superior safety profile in addition to its equivalent efficacy against inflammatory pain. In this figure, the 1.8 mg/mL HA/GlcN/CS group and the 18 mg/mL HA/GlcN/CS group are labeled as "G/C 1.8 mg/ml" and "G/C 18 mg/ml", respectively. The untreated group is labeled as "Untx" in this figure.

Figure 8:
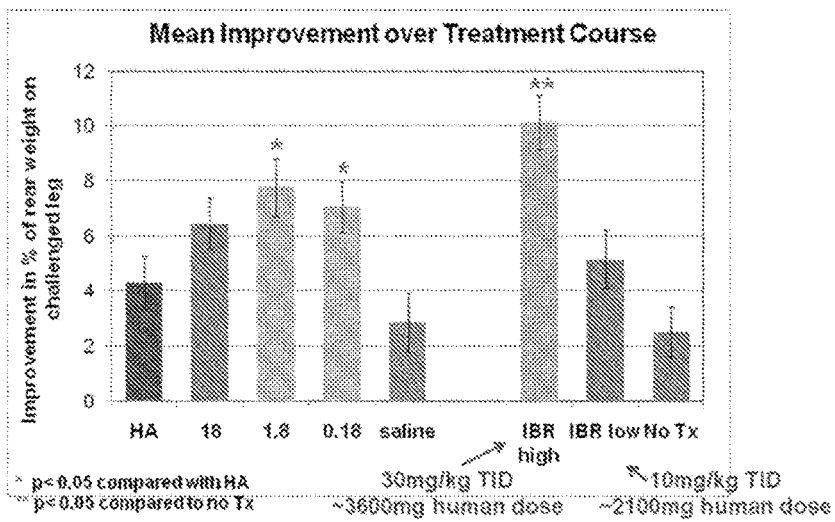
FIG. 8 shows mean improvement results over treatment course in a FCA model of inflammatory arthritis.

In CFA #2 the same protocol was followed except for the lower dose of CFA which was intended to induce a less severe inflammatory reaction and subsequently milder pain. Also, daily oral ibuprofen (labeled as "IBR" in FIG. 8) was used as a positive control rather than diclofenac, at doses of 10 mg/kg and high 30 mg/kg. These doses were equivalent to human daily doses of 2100 and 3600 mg, respectively. Both are considered high doses of ibuprofen that are generally not recommended for long term use. As shown in FIG. 8, it was found that low and medium doses of HA/GlcN/CS gave significant pain reduction compared to HA alone, as measured by cumulative improvement in weight bearing deficiency, whereas the high dose HA/GlcN/CS gave improved pain relief. The high dose of ibuprofen gave significant improvement in pain relief, while the low dose ibuprofen gave a similar result to HA.

PGPS Model of Episodic Inflammatory Arthritis

The PGPS model of arthritis is used to simulate episodic inflammation of the joint. PGPS (peptidoglycan polysaccharide) is a streptococcal cell wall formulation that is injected directly into the joint of the test subject, resulting in a painful inflammatory response. Unlike the continuous FCA response, the inflammatory pain from PGPS is transient, typically lasting only a few days. Following this "priming" injection to the joint, subsequent systemic injections result in inflammatory flares in the previously injected joint for a period of several days. The "reactivation" inflammatory flares can be repeated multiple times, with the inflammatory pain generally decreasing with subsequent reactivation cycles. Alternatively, the joint can be "reprimed" following the initial reactivation, resulting in a more robust inflammatory response in subsequent reactivations.

As with the rat MMT model, the effect of intra-articular therapies is assessed by static weight bearing measurements. It is also useful to conduct a gait analysis of treated animals to assess the effect of treatments on normal function. Gait analysis may reveal functional improvements that are not detectable by weight bearing measurements. In the rat model, gait analysis is done by assessing the paw print pattern of the animal over a defined walking distance. In the present study, the bottom of the rat paw was colored with blue ink, and the dorsal side of the paw was covered in black ink, just prior to the gait analysis measurement. The animal was induced to walk across a sheet of white paper, and gait abnormalities were gauged by assessing the ink patterns compared to untreated animals. For example, a full blue pawprint indicates no pain, a partial blue pawprint indicates limping and black ink on the paper is evidence of foot dragging.

In the present experiment, two reactivation cycles were induced in male Lewis rats following the initial PGPS intra-articular injection. In the first reactivation cycle (beginning on day 0), oral celecoxib and intra-articular dexamethasone (a corticosteroid) were used as positive controls. Weight bearing and gait analysis scores were recorded on days 1, 4, 7, and 14 following the reactivation injection. On day 15, the animals were reprimed with a second IA injection of PGPA, and the second reactivation cycle was initiated 14 days thereafter. For the second reactivation cycle, daily celecoxib and intra-articular triamcinolone were used as positive controls. Weight bearing and gait analysis scores were recorded on days 1, 2, 3, and 4 following reactivation. For both cycles, a single intra-articular injection of an HA/GlcN/CS formulation was administered two hours prior to PGPS reactivation. The following formulations were tested:
HA=15 mg/mL
HA/CS=15 mg/mL/20 mg/mL ("OV/CS 15/20")
HA/CS=15 mg/mL/2 mg/mL ("OV/CS 15/2")
HA/GlcN/CS=15 mg/mL/2 mg/mL/2 mg/mL ("OV/CS/GlcN 15/2/2")
The liquid/solid formulation method described above was used to prepare the test articles.

Figure 9:
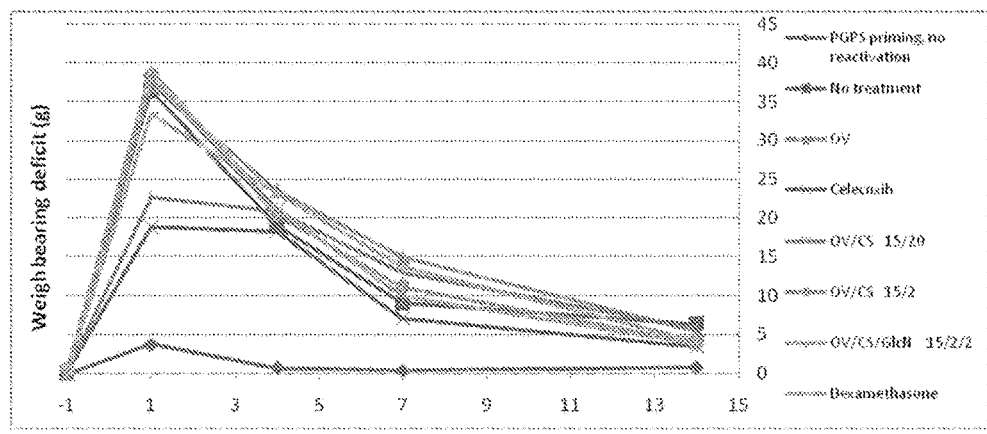
FIG. 9 shows weight bearing deficit results following the first reactivation in a peptidoglycan polysaccharide (PGPS) model of episodic inflammatory arthritis.

Following the first reactivation, only oral celecoxib showed a significant improvement in both weight bearing deficit and gait analysis score on day 1. However, as shown in FIG. 9, the HA/CS 15/20 group showed significant improvement in weight bearing deficit compared to HA alone, and was not statistically different than oral celecoxib on Day 1. By the next time point of the first reactivation cycle (day 4), the pain scores had significantly decreased and there were no significant observed differences between groups.

Figure 10:
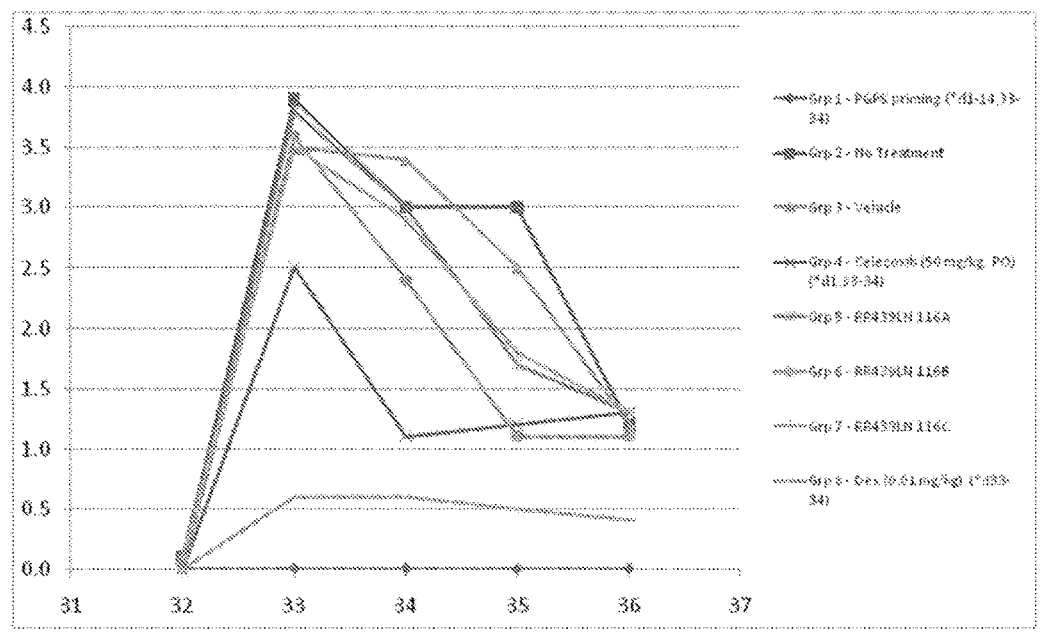
FIG. 10 shows gait analysis score results following the second reactivation in a PGPS model of episodic inflammatory arthritis.

FIG. 10 shows gait analysis score results following the second reactivation. Likely due to the higher level of pain that resulted from the repriming step, only celecoxib and IA triamcinolone gave significant improvement in weight bearing deficit following the second reactivation. On days 2-3, following reactivation (days 34 and 35 of the experiment), HA/CS 15/2 gave significant improvements in gait analysis score, while HA/CS 15/20 gave significant improvement on day 3 after reactivation. In this figure, Grp 5=OV/CS 15/20; Grp 6=OV/CS 15/2; and Grp 7=OV/CS/GlcN 15/2/2.

Figure 11:
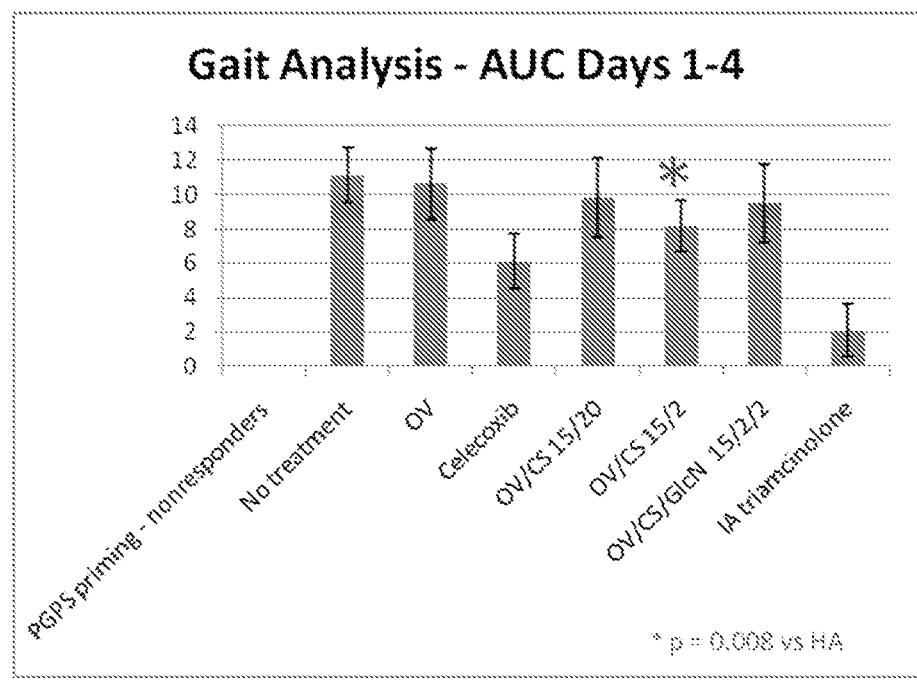
FIG. 11 shows cumulative improvement in gait analysis score results over the first four days following the second reactivation in a PGPS model of episodic inflammatory arthritis.

Over the first four days following the second reactivation, the HA/CS 15/2 group gave a significant cumulative improvement in gait analysis score compared to HA alone. The graph in FIG. 11 shows the cumulative improvement in gait analysis score for the second reactivation. The HA/CS 15/2 group showed significant improvement in gait analysis score.

In summary, these data collectively demonstrated that both lower doses of GlcN and CS ranging from 0.018 mg/ml to 0.18 mg/ml and higher doses of GlcN and CS ranging from 18 mg/ml to 20 mg/ml showed great efficacy in treating joint conditions, such as OA.

Allometric scaling can be used to extrapolate human dosing from animal dosing, based on established relationships between metabolism, body size, and weight in different species. It is common practice to scale up dosing from one species to another by using the ratio of animal weights to the ¾ power:

Dose 2=Dose 1[(weight 2)0.75/(weight 1)0.75], where Dose 2=human dose and Dose 1=rat dose. Typical rat and human weights are 0.3 and 70 kg, respectively. For example, to extrapolate a dose of 1 mg in a rat to human dosing, allometric scaling would predict:

Dose 2=(1 mg)*[(70 kg)0.75/(0.3 kg)0.75]=59.7 mg

For a glucosamine injection concentration of 0.018 mg/ml in a rat, the dose is 0.0009 mg based on an injection volume of 50 The corresponding human dose using the above calculation would be 0.054 mg.

It is common to use volumes ranging from 1-10 ml of solution for intra-articular injection in humans. As such, the necessary glucosamine concentrations for human dosing, corresponding to 0.018 mg/ml in a rat, would be 0.0054-0.054 mg/ml. Using similar calculations for a rat injection concentration of 18 mg/ml, the corresponding human range would be 5.4-54 mg/ml.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A composition for treating a joint, comprising:
an injectable formulation comprising hyaluronic acid (HA), glucosamine, and chondroitin sulfate, and the injectable formulation having a pH in the range of about 3-5.

2. The composition of claim 1, wherein glucosamine is present in a concentration of about 0.005-54 mg/mL.

3. The composition of claim 1, wherein chondroitin sulfate is present in a concentration of about 0.005-54 mg/mL.

4. The composition of claim 1, wherein HA is present in a concentration of about 3.6-36 mg/mL.

5. The composition of claim 1, wherein glucosamine and chondroitin sulfate are present in a ratio by weight of about 1:1.

6. The composition of claim 1, further comprising trehalose.

7. The composition of claim 1, wherein
glucosamine is present in a concentration of about 18-20 mg/mL;
chondroitin sulfate is present in a concentration of about 18-20 mg/mL;
HA is present in a concentration of about 12-17.5 mg/mL;
the pH is in the range of about 3.5-4; and
the osmolality is in the range of about 600-650 mOSM.

8. A method of treating a joint, comprising:
injecting a therapeutically effective amount of a formulation into a joint of a subject,
wherein the formulation comprising hyaluronic acid (HA), glucosamine, and chondroitin sulfate, and having a pH of 3-5.

9. The method of claim 8, further comprising combining the HA with a mixture of the glucosamine and chondroitin sulfate to form the formulation less than about 30 minutes prior to injection.

10. The method of claim 8, wherein glucosamine is present in the formulation in the range of about 0.005-54 mg/mL.

11. The method of claim 8, wherein chondroitin sulfate is present in the formulation in the range of about 0.005-54 mg/mL.

12. The method of claim 8, wherein HA is present in the formulation in the range of about 3.6-36 mg/mL.

13. The method of claim 8, wherein glucosamine and chondroitin sulfate are present in the formulation in a ratio of about 1:1.

14. The method of claim 8, wherein the formulation further comprises trehalose.

15. The method of claim 8, wherein
glucosamine is present in the formulation in the range of about 18-20 mg/mL;
chondroitin sulfate is present in the formulation in the range of about 18-20 mg/mL;
HA is present in the formulation in the range of about 12-17.5 mg/mL;
the pH is in the range of about 3.5-4; and
the osmolality is in the range of about 600-650 mOSM.

16. A kit for treating a joint, comprising:
hyaluronic acid (HA), and glucosamine and chondroitin sulfate separate from the HA, wherein combining the HA, glucosamine, and chondroitin sulfate forms a formulation having a pH in the range of about 3-5; and
a syringe for injecting the formulation into a joint.

17. The kit of claim 16, wherein the syringe comprises
a first chamber containing the HA;
a second chamber containing the glucosamine and chondroitin sulfate, and in fluid communication with the first chamber; and
a plunger configured to displace the glucosamine and chondroitin sulfate from the second container into the first container, to combine the HA, glucosamine, and chondroitin sulfate, and form the formulation.

18. The kit of claim 16, wherein glucosamine has a concentration of about 0.005-54 mg/mL.

19. The kit of claim 16, wherein chondroitin sulfate has a concentration of about 0.005-54 mg/mL.

20. The kit of claim 16, wherein HA has a concentration of about 3.6-36 mg/mL.

\* \* \* \* \*